(12) United States Patent
Niedermeyer

(10) Patent No.: US 12,115,250 B2
(45) Date of Patent: Oct. 15, 2024

(54) USE OF NANOPARTICLES FOR TREATING RESPIRATORY INFECTIONS ASSOCIATED WITH CYSTIC FIBROSIS

(71) Applicant: EVOQ NANO, INC., Salt Lake City, UT (US)

(72) Inventor: William H. Niedermeyer, West Jordan, UT (US)

(73) Assignee: EVOQ NANO, INC., Salt Lake City, UT (US)

( * ) Notice: Subject to any disclaimer, the term of this patent is extended or adjusted under 35 U.S.C. 154(b) by 0 days.

(21) Appl. No.: 16/926,199

(22) Filed: Jul. 10, 2020

(65) Prior Publication Data

US 2021/0007982 A1 Jan. 14, 2021

Related U.S. Application Data

(60) Provisional application No. 62/873,516, filed on Jul. 12, 2019.

(51) Int. Cl.
| | | |
|---|---|---|
| *A61K 9/00* | (2006.01) | |
| *A61K 9/08* | (2006.01) | |
| *A61K 9/14* | (2006.01) | |
| *A61K 9/51* | (2006.01) | |
| *A61K 33/38* | (2006.01) | |
| *A61M 15/00* | (2006.01) | |
| *A61P 11/00* | (2006.01) | |
| *A61P 31/04* | (2006.01) | |

(52) U.S. Cl.
CPC .......... *A61K 9/0078* (2013.01); *A61K 9/5115* (2013.01); *A61K 33/38* (2013.01); *A61M 15/0085* (2013.01); *A61K 9/08* (2013.01)

(58) Field of Classification Search
CPC .... A61K 9/0078; A61K 9/5115; A61K 33/38; A61K 9/08; A61K 9/14; A61K 9/008; A61M 15/0085; A61P 31/04; A61P 11/00; Y02A 50/30
See application file for complete search history.

(56) References Cited

U.S. PATENT DOCUMENTS

| | | | |
|---|---|---|---|
| 3,133,023 A | 5/1964 | Vogel | |
| 4,121,017 A | 10/1978 | Dougherty et al. | |
| 4,515,740 A | 5/1985 | Schuettenberg et al. | |
| 5,047,448 A | 9/1991 | Tanaka et al. | |
| 5,227,608 A | 7/1993 | Yoshida et al. | |
| 5,390,864 A | 2/1995 | Alexander | |
| 5,585,020 A | 12/1996 | Becker et al. | |
| 5,677,075 A | 10/1997 | Fujita | |
| 6,051,279 A | 4/2000 | Gualco et al. | |
| 6,232,264 B1 | 5/2001 | Lukehart et al. | |
| 6,239,453 B1 | 5/2001 | Yamada et al. | |
| 6,509,070 B1 | 1/2003 | Voevodin et al. | |
| 6,660,379 B1 | 12/2003 | Lakowicz et al. | |
| 6,720,006 B2 | 4/2004 | Hanke et al. | |
| 7,014,737 B2 | 3/2006 | Harutyunyan et al. | |
| 7,252,814 B2 | 8/2007 | De et al. | |
| 7,332,351 B2 | 2/2008 | Tan et al. | |
| 7,371,457 B2 | 5/2008 | Oldenburg et al. | |
| 7,374,730 B2 | 5/2008 | Simard et al. | |
| 7,384,560 B2 | 6/2008 | Martens et al. | |
| 7,449,679 B2 | 11/2008 | Plewa et al. | |
| 7,509,993 B1 | 3/2009 | Turng et al. | |
| 7,527,824 B2 | 5/2009 | Becker et al. | |
| 7,553,801 B2 | 6/2009 | Alexander et al. | |
| 7,625,637 B2 | 12/2009 | Kim | |
| 7,662,731 B2 | 2/2010 | Itoh et al. | |
| 7,682,970 B2 | 3/2010 | Grigoropoulos et al. | |
| 7,700,032 B1 | 4/2010 | Lu et al. | |
| 7,884,160 B2 | 2/2011 | Wang et al. | |
| 7,967,876 B2 | 6/2011 | Aradi et al. | |
| 7,985,367 B2 | 7/2011 | Hiromatsu et al. | |
| 8,097,233 B2 | 1/2012 | Porterat | |
| 8,435,602 B1 | 5/2013 | Seal | |
| 8,490,583 B1 | 7/2013 | Gardenier | |
| 8,490,586 B2 | 7/2013 | Ross et al. | |
| 8,524,139 B2 | 9/2013 | Toth et al. | |
| 8,685,293 B1 | 4/2014 | Coppa et al. | |

(Continued)

FOREIGN PATENT DOCUMENTS

| | | |
|---|---|---|
| CA | 2560837 A1 | 3/2007 |
| CN | 101128550 A | 2/2008 |

(Continued)

OTHER PUBLICATIONS

Pompilio et al., Electrochemically synthesized silver nanoparticles are active against planktonic and biofilm cells of Pseudomonas aeurginosa and other cystic fibrosis-associated bacterial pathogens, Frontiers in Microbiology, vol. 9, Article 1349, pp. 1-11. (Year: 2018).*

Klinger-Strobel et al., Aspects of pulmonary drug delivery strategies for infections in cystic fibrosis-Where do we stand ?; Expert Opinion, Drug Delivery, 2015, 12(8); 1351-1374 (Year: 2015).*

Office Action received for U.S. Appl. No. 14/861,243, mailed on Sep. 25, 2017.

Office Action received for U.S. Appl. No. 14/861,318, mailed on Apr. 25, 2016.

Office Action received for U.S. Appl. No. 14/861,375 mailed on Apr. 3, 2018.

Office Action received for U.S. Appl. No. 14/861,375, mailed on Sep. 8, 2017.

(Continued)

*Primary Examiner* — Mina Haghighatian
(74) *Attorney, Agent, or Firm* — Workman Nydegger

(57) ABSTRACT

This disclosure relates to metal nanoparticle compositions and methods for treating respiratory infections associated with cystic fibrosis. An amount of nonionic, ground state metal nanoparticles are administered to a patient via inhalation. The metal nanoparticles have properties that enable effective transport through the viscous mucus layer to the epithelia and surrounding tissues, killing or deactivating infecting microbes at the targeted respiratory tissue and throughout the overlying mucus layer.

20 Claims, 11 Drawing Sheets

(56) References Cited

U.S. PATENT DOCUMENTS

| | | |
|---|---|---|
| 8,709,531 B2 | 4/2014 | Miller |
| 8,802,234 B2 | 8/2014 | Che et al. |
| 8,883,865 B2 | 11/2014 | Difrancesco et al. |
| 8,992,815 B2 | 3/2015 | Hu et al. |
| 9,259,407 B2 | 2/2016 | Baker et al. |
| 9,434,006 B2 | 9/2016 | Niedermeyer |
| 9,463,510 B2 | 10/2016 | Hendi et al. |
| 9,512,377 B2 | 12/2016 | Binder et al. |
| 9,627,713 B2 | 4/2017 | Moganty et al. |
| 9,839,652 B2 | 12/2017 | Tarbet et al. |
| 9,849,512 B2 | 12/2017 | Niedermeyer |
| 9,883,670 B2 | 2/2018 | Niedermeyer |
| 9,885,001 B2 | 2/2018 | Niedermeyer |
| 10,099,191 B1 | 10/2018 | Lu et al. |
| 2001/0031564 A1 | 10/2001 | Suzuki et al. |
| 2002/0051823 A1 | 5/2002 | Yan et al. |
| 2003/0012686 A1 | 1/2003 | Andresen et al. |
| 2003/0086859 A1 | 5/2003 | Kawakami et al. |
| 2003/0102099 A1 | 6/2003 | Yadav et al. |
| 2003/0108612 A1 | 6/2003 | Xu et al. |
| 2003/0129320 A1 | 7/2003 | Yu |
| 2003/0228525 A1 | 12/2003 | Kozawa et al. |
| 2004/0103936 A1 | 6/2004 | Andriessen |
| 2004/0176312 A1* | 9/2004 | Gillis ............... A61P 17/06 514/36 |
| 2004/0214001 A1 | 10/2004 | Oldenburg et al. |
| 2005/0061779 A1 | 3/2005 | Blumenfeld et al. |
| 2005/0061785 A1 | 3/2005 | Schroder et al. |
| 2005/0153071 A1 | 7/2005 | Bouvrette et al. |
| 2005/0158506 A1 | 7/2005 | Waki et al. |
| 2005/0247866 A1 | 11/2005 | Plewa et al. |
| 2005/0258149 A1 | 11/2005 | Glukhoy et al. |
| 2005/0260276 A1 | 11/2005 | Yang et al. |
| 2006/0049034 A1 | 3/2006 | Lee et al. |
| 2006/0142853 A1 | 6/2006 | Wang et al. |
| 2007/0003603 A1 | 1/2007 | Karandikar et al. |
| 2007/0029185 A1 | 2/2007 | Tung |
| 2007/0125196 A1 | 6/2007 | Zhong et al. |
| 2007/0140951 A1 | 6/2007 | O'Brien et al. |
| 2007/0141259 A1 | 6/2007 | House et al. |
| 2007/0207335 A1 | 9/2007 | Karandikar et al. |
| 2007/0269576 A1 | 11/2007 | Barton et al. |
| 2007/0287202 A1 | 12/2007 | Maehashi et al. |
| 2008/0006524 A1 | 1/2008 | Liu et al. |
| 2008/0035682 A1 | 2/2008 | Coffey et al. |
| 2008/0044148 A1 | 2/2008 | Robinson et al. |
| 2008/0050448 A1 | 2/2008 | Wilson et al. |
| 2008/0143021 A1 | 6/2008 | Ehrentraut et al. |
| 2008/0161631 A1 | 7/2008 | Axtell et al. |
| 2008/0241490 A1 | 10/2008 | Newman et al. |
| 2008/0263940 A1 | 10/2008 | Parish et al. |
| 2008/0292673 A1 | 11/2008 | Crudden |
| 2009/0000186 A1 | 1/2009 | Sanders et al. |
| 2009/0028947 A1 | 1/2009 | Rahman Nia |
| 2009/0039316 A1 | 2/2009 | Hirai et al. |
| 2009/0061230 A1 | 3/2009 | Berkei et al. |
| 2009/0104179 A1 | 4/2009 | Boyden et al. |
| 2009/0117268 A1 | 5/2009 | Lewis et al. |
| 2009/0148484 A1 | 6/2009 | Lin et al. |
| 2009/0175948 A1 | 7/2009 | Jiang et al. |
| 2009/0191288 A1 | 7/2009 | Squires |
| 2009/0214766 A1 | 8/2009 | Magdassi et al. |
| 2009/0246530 A1 | 10/2009 | Murakami et al. |
| 2010/0040655 A1 | 2/2010 | Ren et al. |
| 2010/0050872 A1 | 3/2010 | Lee |
| 2010/0068299 A1 | 3/2010 | Van et al. |
| 2010/0072645 A1 | 3/2010 | Hiromatsu et al. |
| 2010/0080957 A1 | 4/2010 | Chinn et al. |
| 2010/0092367 A1 | 4/2010 | Porterat |
| 2010/0154591 A1 | 6/2010 | Islam |
| 2010/0167958 A1 | 7/2010 | Lin et al. |
| 2010/0172997 A1 | 7/2010 | Omary et al. |
| 2010/0180413 A1 | 7/2010 | Jeong |
| 2010/0183739 A1 | 7/2010 | Newman |
| 2010/0187091 A1 | 7/2010 | Pierce et al. |
| 2010/0196192 A1 | 8/2010 | Liu et al. |
| 2010/0212221 A1 | 8/2010 | Aradi |
| 2010/0255110 A1 | 10/2010 | Yoon et al. |
| 2010/0272650 A1 | 10/2010 | Tsukada et al. |
| 2010/0272770 A1 | 10/2010 | De et al. |
| 2010/0301013 A1 | 12/2010 | Conneely et al. |
| 2011/0039078 A1 | 2/2011 | Brennan et al. |
| 2011/0052460 A1 | 3/2011 | Coffey et al. |
| 2011/0129536 A1 | 6/2011 | Donati et al. |
| 2011/0155643 A1 | 6/2011 | Tov et al. |
| 2011/0192450 A1 | 8/2011 | Liu et al. |
| 2011/0193025 A1 | 8/2011 | Ichikawa et al. |
| 2011/0196044 A1 | 8/2011 | Hu et al. |
| 2011/0197369 A1 | 8/2011 | Hinestroza et al. |
| 2011/0201527 A1 | 8/2011 | Lin et al. |
| 2011/0206753 A1 | 8/2011 | Karpov et al. |
| 2011/0228890 A1 | 9/2011 | Dean et al. |
| 2011/0244056 A1 | 10/2011 | Santra |
| 2011/0297653 A1 | 12/2011 | Ehrentraut et al. |
| 2012/0088066 A1 | 4/2012 | Aytug et al. |
| 2012/0094036 A1 | 4/2012 | Droege et al. |
| 2012/0124899 A1 | 5/2012 | Difrancesco et al. |
| 2012/0136164 A1 | 5/2012 | Ying et al. |
| 2012/0138347 A1 | 6/2012 | Bahnmueller et al. |
| 2012/0138862 A1 | 6/2012 | Hogan |
| 2012/0164073 A1 | 6/2012 | Xu et al. |
| 2012/0174472 A1 | 7/2012 | Mills |
| 2012/0183674 A1 | 7/2012 | Bonn-Savage et al. |
| 2012/0301528 A1 | 11/2012 | Uhlmann et al. |
| 2012/0301531 A1 | 11/2012 | Uhlmann et al. |
| 2012/0313200 A1 | 12/2012 | Jackrel et al. |
| 2012/0328701 A1 | 12/2012 | Edelson et al. |
| 2013/0001833 A1 | 1/2013 | Niedermeyer |
| 2013/0078510 A1 | 3/2013 | Reynolds et al. |
| 2013/0116369 A1 | 5/2013 | Qi et al. |
| 2013/0152823 A1 | 6/2013 | Fouda et al. |
| 2013/0203849 A1 | 8/2013 | Ben Yehuda |
| 2013/0224477 A1 | 8/2013 | Xu et al. |
| 2013/0273116 A1 | 10/2013 | Jespersen et al. |
| 2013/0334104 A1 | 12/2013 | Halas et al. |
| 2013/0337998 A1 | 12/2013 | Irving et al. |
| 2014/0024026 A1 | 1/2014 | Alocilja et al. |
| 2014/0178513 A1 | 6/2014 | Matthews |
| 2014/0186290 A1* | 7/2014 | Chin ................ B82Y 5/00 424/78.31 |
| 2014/0221543 A1 | 8/2014 | Wang et al. |
| 2014/0274830 A1 | 9/2014 | Pol et al. |
| 2014/0288194 A1 | 9/2014 | Niedermeyer |
| 2014/0322351 A1 | 10/2014 | Gawande et al. |
| 2014/0370293 A1 | 12/2014 | Johnson |
| 2015/0008313 A1 | 1/2015 | Oboda et al. |
| 2015/0030919 A1 | 1/2015 | Kozawa et al. |
| 2015/0066135 A1 | 3/2015 | Weber et al. |
| 2015/0190550 A1 | 7/2015 | Nusko et al. |
| 2016/0081346 A1 | 3/2016 | Niedermeyer |
| 2016/0081347 A1 | 3/2016 | Niedermeyer |
| 2016/0082513 A1 | 3/2016 | Niedermeyer |
| 2016/0082514 A1 | 3/2016 | Niedermeyer |
| 2016/0083146 A1 | 3/2016 | Han |
| 2016/0083665 A1 | 3/2016 | Niedermeyer |
| 2016/0083901 A1 | 3/2016 | Niedermeyer |
| 2016/0144350 A1 | 5/2016 | Aizenberg et al. |
| 2016/0287631 A1* | 10/2016 | Tarbet ............... A61K 33/244 |
| 2016/0298243 A1 | 10/2016 | Tarbet et al. |
| 2016/0372243 A1 | 12/2016 | Cassignol et al. |
| 2017/0129975 A1 | 5/2017 | Hallinan et al. |
| 2017/0136112 A1 | 5/2017 | Pillich et al. |
| 2017/0166485 A1 | 6/2017 | Hong et al. |
| 2017/0209490 A1 | 7/2017 | Niedermeyer |
| 2018/0028417 A1* | 2/2018 | Koo ................ A61K 8/73 |
| 2018/0078580 A1 | 3/2018 | Tarbet et al. |
| 2018/0126463 A1 | 5/2018 | Niedermeyer |
| 2018/0282852 A1 | 10/2018 | Soloway |

(56) References Cited

U.S. PATENT DOCUMENTS

| | | | | |
|---|---|---|---|---|
| 2018/0368417 | A1* | 12/2018 | Niedermeyer | ....... A61K 33/243 |
| 2019/0225498 | A1 | 7/2019 | Ruiz et al. | |

FOREIGN PATENT DOCUMENTS

| | | |
|---|---|---|
| CN | 101180372 A | 5/2008 |
| CN | 101415644 A | 4/2009 |
| CN | 101716684 A | 6/2010 |
| CN | 101932752 A | 12/2010 |
| CN | 101960070 A | 1/2011 |
| CN | 102120619 A | 7/2011 |
| CN | 102753628 A | 10/2012 |
| CN | 103796946 A | 5/2014 |
| CN | 103891558 A | 7/2014 |
| CN | 104014811 A | 9/2014 |
| DE | 102005044360 A1 | 3/2007 |
| EP | 2140958 A2 | 1/2010 |
| EP | 2559436 A1 | 2/2013 |
| JP | 2008-527169 | 7/2008 |
| JP | 2010-001528 A | 1/2010 |
| KR | 2006-0021749 A | 3/2006 |
| WO | 2006/026026 A2 | 3/2006 |
| WO | 2006/053225 A2 | 5/2006 |
| WO | 2006/062826 A2 | 6/2006 |
| WO | 2006/126823 A1 | 11/2006 |
| WO | 2008/043396 A1 | 4/2008 |
| WO | 2008/153239 A1 | 12/2008 |
| WO | 2009/025955 A1 | 2/2009 |
| WO | 2009/044146 A1 | 4/2009 |
| WO | 2009/046081 A2 | 4/2009 |
| WO | 2009/066011 A2 | 5/2009 |
| WO | 2009/091900 A1 | 7/2009 |
| WO | 2011/045627 A1 | 4/2011 |
| WO | 2012/082364 A1 | 6/2012 |
| WO | 2013/006430 A2 | 1/2013 |
| WO | 2013/141879 A1 | 9/2013 |
| WO | 2014/066850 A2 | 5/2014 |
| WO | 2014/096556 A2 | 6/2014 |
| WO | 2014/137352 A1 | 9/2014 |
| WO | 2014/190097 A1 | 11/2014 |
| WO | 2016/007112 A1 | 1/2016 |
| WO | 2016/007113 A1 | 1/2016 |

OTHER PUBLICATIONS

Office Action received for U.S. Appl. No. 14/861,442, mailed on Aug. 23, 2017.

Office Action received for U.S. Appl. No. 14/861,442, mailed on Feb. 22, 2017.

Office Action received for U.S. Appl. No. 14/861,442, mailed on Sep. 29, 2016.

Office Action received for U.S. Appl. No. 14/861,562, mailed on Dec. 7, 2016.

Office Action received for U.S. Appl. No. 14/861,562, mailed on Jun. 23, 2017.

Office Action received for U.S. Appl. No. 15/088,863, mailed on Feb. 3, 2017.

Office Action received for U.S. Appl. No. 15/088,863, mailed on Jul. 11, 2017.

Office Action received for U.S. Appl. No. 15/098,071, mailed on Aug. 8, 2019.

Office Action received for U.S. Appl. No. 15/415,562, mailed on Jan. 31, 2018.

Office Action received for U.S. Appl. No. 15/415,562, mailed on Jun. 20, 2018.

Office Action received for U.S. Appl. No. 15/415,562, mailed on May 23, 2017.

Office Action received for U.S. Appl. No. 15/415,562, mailed on Sep. 5, 2017.

Office Action received for U.S. Appl. No. 15/825,912, mailed on Jul. 15, 2019.

Office Action received for U.S. Appl. No. 16/012,508, mailed on Dec. 11, 2018.

Office Action received for U.S. Appl. No. 16/012,508, mailed on May 31, 2019.

Pal et al. (Applied and Environmental Microbiology 2007;73(6):1712-1720) (Year: 2007).

Pan et al. "Hybrid Electrolytes with Controlled Network Structures for Lithium Metal Batteries", Adv. Mater., 2015; 27:5995-6001.

Phuoc et al., "Synthesis of Ag-deoionized water nanofluids using multi-beam laser ablation in fluids", Optics and Lasers in Engineering 45 (2007) 1099-1106.

Prabhu, S. et al. "Silver nanoparticles: mechanism of antimicrobial action, synthesis, medical applications, and toxicity effects" International Nano Letters 2012, 2:32, pp. 1-10.

Rawashdeh et al., "Antibacterial Mechanisms of Metallic Nanoparticles: A Review", Dynamic Biochemistry, Process Biotechnology and Molecular Biology 2009 pp. 12-20.

Rhim, J-W. et al. "Preparation and characterization of bio-nanocomposite films of agarand silver nanoparticles: Laser ablation method" Carbohydrate Polymers 103 (2014) 456065 (Year: 2014).

Riabinina et al., "Influence of pressure on the Pt nanoparticle growth modes during pulsed laser ablation," Journal of Applied Physics 108, 034322 (2010, published online Aug. 12, 2010).

Sahu et al., "Flower Shaped Silver Nanostructures: An Efficient Bacteria Exterminator", A Search forAntibacterial Agents; Chapter 2; [online] retrieved from:http://www.intechopen.com/books/a-search-forantibacterial-agents; 2007; 73(6): 1712-1720 (Year: 2007).

Samberg et al. (Nanotoxicology 2011 ;5(2):244-253) (Year: 2011).

Santos et al., "Enhancement of antibiotic effect via gold:silver-alloy nanoparticles", J. Nanopart Res (2012) 14:859, pp. 1-8.

Sweeney et al., "Rapid Purification and Size Separation of Gold Nanoparticles via Diafiltration", J. Am. Chem. Soc. 2006, 128, 3190-3197 (Published on web Feb. 18, 2006).

Sylvestre et al., "Surface Chemistry of Gold Nanoparticles Produced by Laser Ablation in Aqueous Media", J Phys. Chem. B 2004, 108, 16864-16869.

Thanaa Majied Al-Nori, "Antibacterial activity of Silver and Gold Nanoparticles against *Streptococus Staphylococcus aureus* and *E.coli*", Al—Mustansiriya J. Sci, Vo. 23, No. 3, 2012.

Theodorou et al., "Inhalation of Silver Nanomaterials—Seeing the Risks", International Journal of Molecular Sciences, 2014, 15, 23936-23974.

Tu et al. "Nanoporous Polymer-Ceramic Composite Electrolytes for Lithium Metal Batteries", Adv. Energy Mater., 2014;4: 1300654.

U.S. Appl. No. 13/175,708, Notice of Allowance cited in U.S. Appl. No. 13/175,708 dated Aug. 21, 2017.

U.S. Appl. No. 13/175,708, filed Jul. 1, 2011, Final Office Action dated Mar. 28, 2016.

U.S. Appl. No. 14/861,243, filed Sep. 22, 2015, Office Action dated Mar. 9, 2016.

Xiang Dongxi, "Study of Silver—nanoparticles on antiviral action", Journal of Dalian Medical University, vol. 31, No. 6, 2009.

Xinxia Yue, et al., "Preparation of silver nanoparticles by tea extracts and its application in the antibacterial finishing of cotton fabric", 2014, Shanghai Textile Science & Technology, vol. 42, No. 5, p. 45-49.

Yuteng Wan et al., "Modification of coral-like SnO2 nanostructures with dense TiO2 nanoparticles for a self-cleaning gas sensor", Talanta, vol. 99, pp. 394-403.

Agnihotri, Shekar, et al., "Immobilized silver nanoparticles enhance contact killing and show highest efficacy: elucidation of the mechanism of bacterial action of silver," Nanoscale, 2013. published Jan. 3, 2013. (Year: 2013).

Badawy et al., "Surface Charge-Dependent Toxicity of Silver Nanoparticles", Environ. Sci. Technol. 2011, 45, 283-287.

Barcikowski et al., "Generation of nanoparticle colloids by picosecond and femtosecond laser ablations in liquid flow", Appl. Phys. Lett. 91, 083113 (2007).

Chien et al., "Synthesis of nanoparticles: sunlight formation of gold nanodecahedra for ultra-sensitive lead-ion detection", Green Chem., vol. 13, pp. 1162-1166, May 2011.

(56) References Cited

OTHER PUBLICATIONS

Choudhury et al. "A highly reversible room-temperature lithium metal battery based on crosslinked hairy nanoparticles", Nature Communications, 2015; DOI: 10.1038/ncomms10101.
Cox (https://microbiologysociety.org/blog/rabies-virus-can-we-treat-the-untreatable.html) Jun. 25, 2019, pp. 1-4 (Year:2019).
Daissy Paredes, et al., "Synthesis, characterization, and evaluation of antibacterial effect of Ag nanoparticles against *Escherichia coli* 0157:h7 and methicillin-resistant *Staphylococcus aureus* (Mrsa)", Apr. 3, 2014, International Journal of Nanomedicine, p. 1717-1729.
Gogoi et al. (Langmuir 2006;22:9322-9328) (Year: 2006).
Guangnian Xu, et al. "Progress in preparation of nano-silver", 2019, Materials Review, vol. 24, No. 11, p. 139-142.
Gurevitch et al. "Nanocomposites of Titanium Dioxide and Polystyrene-Poly(ethylene oxide) Block Copolymer as Solid- State Electrolytes for Lithium Metal Batteries", Journal of The Electrochemical Society, 2013; 160(9): A1611-A1617.
Hamm et al. "Ionic conductivity enhancement of sputtered gold nanoparticle-in-ionic liquid electrolytes", J Mater Chem A, 2014; 2(3): 792-803.
He et al. "Ionic liquid and nanoparticle hybrid systems: Emerging applications", 2017. Advances in Colloid and Interface Science, 2017; 244: 54-70.
Hopp Bela et al., "Production of nanostructures on bulk metal samples by laser ablation for fabrication of low-reflective surfaces", applied physics a materials science & processing, Springer Berlin Heidelberg.
Hultin, "A Guide to Solvents and Reagents in Introductory Organic Chemistry for students in 2.222", Obtained from https://home.cc.umanitoba.ca/hultin/chem2220/Support/solvents_and_reagent- s.pdf on Jan. 25, 2018, originally published Feb. 12, 2002—17 pages.
International Coral Reef Initiative, "What are Corals", downloaded from http://www.iciforum.org/about-coral-reefs/what-are-corals on Sep. 5, 2017.
International Search Report and Written Opinion received for PCT Patent Application No. PCT/US2020/041796, mailed on Oct. 7, 2020, 9 pages.
International Search Report for PCT Aoo. No. PCT/US2015/051639 dated Dec. 17, 2015.
International Search Report for PCT App. No. PCT/US2012/044907 dated Jan. 13, 2013.
International Search Report for PCT App. No. PCT/US2015/051640 dated Dec. 17, 2015.
International Search Report for PCT App. No. PCT/US2015/051642 dated Dec. 14, 2015.
International Search Report for PCT App. No. PCT/US2015/051643 dated Dec. 17, 2015.
International Search Report for PCT App. No. PCT/US2015/051646 dated Dec. 18, 2015.
International Search Report for PCT App. No. PCT/US2015/051649 dated Dec. 17, 2015.
Jacobson, R. Inside Energy Oct. 2014; [online] retrieved on Jan. 29, 2017 from: http://www.pbs.org/newshour/updates/six-diseases-actually-worry/; 10 pages.
Jana et al., "Seeding Growth for Size Control of 5-40 nm Diameter Gold Nanoparticles", Langmuir 2001, 17, 6782-6786.
Kewal K. Jain Md, Fracs, Ffpm., "The Handbook of Nanomedicine" Humana Press, 2008.
Korf et al. "Piperidine tethered nanoparticle-hybrid electrolyte for lithium metal batteries", J Mater. Chem., 2014; 2: 11866-11873.
Leisure Pro, "Coral Identification: Types of Coral (Part 1-Hard Coral)", downloaded from http://www.leisurepro.com/blog/explorethe- blue/coral-identification-types-of-coral-part-1 on Sep. 2017.
Liu et al., "A novel coral-like porous SnO2 hollow architecture: biomimetic swallowing growth mechanism and enhanced photovoltaic property for dye-sensitized solar cell application", Chem. Commun., vol. 46, pp. 472-474, 2010.
Lu et al. "Ionic-Liquid-Nanoparticle Hybrid Electrolytes: Applications in Lithium Metal Batteries", Angew. Chem. Int. Ed., 2014; 53: 488-492.
Mafune et al., "Formation of Stable Platinum Nanoparticles by Laser Ablation in Water", J. Phys. Chem. B 2003, 107, 4218-4223.
Malvern, "The use of the Malvern Zetasizer for the measurement of Zeta Potential", article from the Internet, http://www.malvern.co.alLaboratory/zetaintm.htm 10 pages, printed on Feb. 12, 2002.
Muller, M. "Bacterial Silver Resistance Gained by Cooperative Interspecies Redox Behavior" Antimicrobial Agents and Chemotherapy 2018, 62 (8), 1-10 (Year: 2018).
Mycozil, "The Benefits of Colloidal Silver for Toenail Fungus", http://www.nailfungustoenail.com/benefitsofcolloidalsilverfortoenailfungu- s.html.
Naftulin (https://www.sciencealert.com/a-deadly-fungus-is-spreading-across-the-worid-and-we-don-t-know-how-to-stop-it) Apr. 9, 2019, pgs (Year: 2019).
Nakashima et al. "Preparation of fusion materials based on ionic liquids and cationic gold nanoparticles", Polymer Journal, 2015; 47: 171-176.
NOAA Ocean Service Education, "Corals", downloaded from https://oceanservice.noaa.gov/education/kits/corals/coral03 growth.html on Sep. 5, 2017.
Non-Final Office Action received for U.S. Appl. No. 15/825,912, mailed on Aug. 17, 2020, 36 pages.
Notice of Allowance received for U.S. Appl. No. 14/861,318, mailed on Jun. 15, 2016.
Notice of Allowance received for U.S. Appl. No. 14/861,318, mailed on May 20, 2016.
Office Action received for U.S. Appl. No. 13/175,708, mailed on Feb. 10, 2017.
Office Action received for U.S. Appl. No. 13/175,708, mailed on Jul. 6, 2015.
Office Action received for U.S. Appl. No. 13/175,708, mailed on May 30, 2014.
Office Action received for U.S. Appl. No. 13/175,708, mailed on Nov. 13, 2014.
Office Action received for U.S. Appl. No. 14/298,594, mailed on Mar. 21, 2017.
Office Action received for U.S. Appl. No. 14/298,594, mailed on Oct. 17, 2017.
Office Action received for U.S. Appl. No. 14/861,243, mailed on Feb. 2, 2018.
Office Action received for U.S. Appl. No. 14/861,243, mailed on Jan. 27, 2017.
Office Action received for U.S. Appl. No. 14/861,243, mailed on Jul. 26, 2016.
Office Action received for U.S. Appl. No. 14/861,243, mailed on Nov. 2, 2016.

\* cited by examiner

USE OF NANOPARTICLES FOR TREATING RESPIRATORY INFECTIONS ASSOCIATED WITH CYSTIC FIBROSIS

CROSS-REFERENCE TO RELATED APPLICATIONS

This application claims priority to and the benefit of U.S. Provisional Patent Application Ser. No. 62/873,516, filed Jul. 12, 2019, which is incorporated herein by this reference in its entirety.

BACKGROUND

Cystic fibrosis is an inherited condition where the cystic fibrosis transmembrane conductance regulator (CFTR) proteins become dysfunctional due to mutations in the CFTR gene. Without proper CFTR protein function, mucus in various organs becomes thick, sticky, and difficult to properly clear. In the respiratory system, and particularly in the lungs, the thick mucus tends to gather and trap bacteria and other microbes, leading to frequent and/or chronic respiratory infections.

Cystic fibrosis patients are prone to lung infections from multiple infections microbial agents, including known drug resistant bacteria such as *Burkholderia cepacia* and *Pseudomonas aeruginosa* species. These infections are challenging to treat in cystic fibrosis patients due to the viscous mucus that accumulates in the central airways. Once infected, cystic fibrosis patients are at risk of experiencing a rapid decline in lung function that can lead to severe lung disease and possibly death.

Conventional antibiotics cannot easily penetrate the thick mucus, so administration via inhalation often fails to reach the underlying respiratory tissue. On the other hand, systemic administration of antibiotics may eventually reach infected epithelia, but because more bacteria reside within the thick overlying mucus, reinfection readily occurs.

Accordingly, there is an ongoing need for compositions and methods for treating respiratory conditions associated with cystic fibrosis, and in particular for compositions and methods capable of effectively treating drug resistant bacterial infections commonly affecting cystic fibrosis patients.

BRIEF SUMMARY

This disclosure is directed to compositions and methods for treating respiratory infections, and in particular embodiments for treating respiratory infections associated with cystic fibrosis. In one embodiment, a treatment composition comprises a plurality of nonionic, ground state, spherical nanoparticles with no external edges or bond angles mixed in or mixable within a carrier formulated for administration to a patient via inhalation.

The treatment compositions described herein are able to effectively penetrate thick, viscous mucus layers to reach targeted microbes within the mucus and to reach underlying respiratory tissue. This beneficially allows the treatment composition to reach and treat underlying infected respiratory tissue. In addition, it allows the treatment composition to reach bacteria within the mucus and associated biofilm layers in which the bacteria tend to lie in wait shielded from conventional antibiotics. Notwithstanding the effective penetrative abilities of the nanoparticles of the treatment compositions described herein, they are also capable of being effectively cleared from the patient through normal clearance routes and thereby avoid building up within the treated respiratory tissue or other tissues or organs of the body.

In one embodiment, a method of treating a respiratory infection comprises administering the nanoparticle treatment composition to a patient via inhalation, and the treatment composition treating the respiratory infection. The infection may be, for example, caused by one or more antibiotic resistant bacteria. The treatment composition is beneficially able to kill or deactivate bacteria associated with the infection without harming respiratory epithelia and other nearby tissues.

The metal nanoparticles kill bacteria without significant release of silver (Ag+) or other metal ions. Because the metal nanoparticles do not release significant quantities of silver or other metal ions, they are essentially non-toxic to humans and other animals (i.e., whatever amount or concentration of ions, if any, that are released from the metal nanoparticles is/are below a threshold toxicity level at which they become toxic to humans, other mammals, birds, reptiles, fish, and amphibians).

In some embodiments, the nanoparticles are spherical and have a mean diameter of about 1 nm to about 40 nm, or about 2 nm to about 20 nm, or about 3 nm to about 15 nm, or about 4 nm to about 12 nm, or about 6 nm to about 10 nm, or a size range with endpoints defined by any two of the foregoing values. Nanoparticles within these size ranges, in particular nanoparticles having a mean diameter of about 8 nm, have been found to effectively penetrate mucus while still being capable of effective clearance from the patient's body (e.g., via the lymphatic system and kidneys).

The nanoparticles may be provided in an amount such that when mixed with the carrier, the nanoparticles have a concentration of about 10 ppb to about 100 ppm, or about 50 ppb to about 50 ppm, or about 200 ppb to about 20 ppm, or about 500 ppb to about 10 ppm, or about 1 ppm, or a concentration within a range defined by any two of the foregoing values.

Within these concentration ranges, the nanoparticles have been found to be effective in killing or deactivating targeted microbes. Beneficially, because the nanoparticles are effective even at relatively low concentrations, more dilute doses may be administered (and/or less nanoparticles may be dosed overall), which lowers the clearance burden on the body and reduces the risk of unwanted side-effects such as harm to the patient's own cells/tissues or systemic harm to other beneficial microbiota of the patient.

The treatment composition may be administered using any suitable inhalation route, including through the use of a metered-dose inhaler, a nebulizer, and/or a dry powder dispersion device. These types of devices typically include a mouthpiece or facemask enabling transfer of nebulized/atomized medicament to the patient. A nebulizer may be an ultrasonic nebulizer, a jet nebulizer, a vibrating mesh nebulizer, or a soft mist inhaler, for example.

The treatment compositions have shown versatile efficacy in treating a wide variety of bacteria, including several problematic bacterial strains that have resistance to one or more conventional antibiotics.

DETAILED DESCRIPTION

Introduction

Figure 1A:
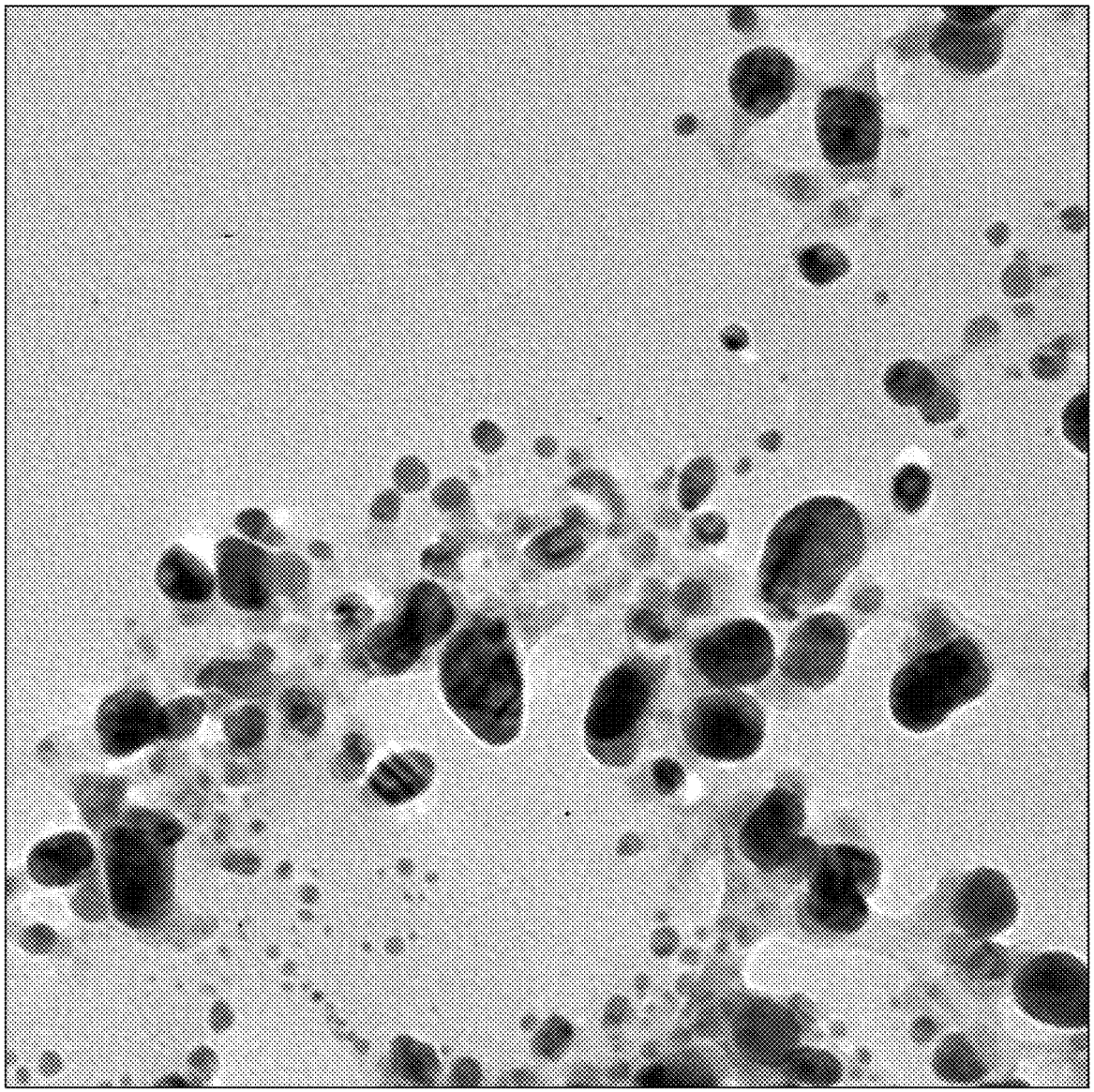
FIGS. 1A-1D show TEM images of various non-spherical nanoparticles (i.e., that have surface edges and external bond angles) made according to conventional chemical synthesis or electrical discharge methods.

The present disclosure is directed to compositions and methods for treating respiratory infections, and in particular for treating respiratory infections associated with cystic fibrosis. In one embodiment, a treatment composition comprises a plurality of nonionic, ground state, spherical nanoparticles with no external edges or bond angles mixed in or mixable within a carrier formulated for administration to a patient via inhalation.

Although the present disclosure will often describe treatment of bacteria specifically, it will be understood that the same compositions and methods may additionally or alternatively be utilized to treat respiratory conditions that involve a viral and/or fungal infection, and the nanoparticle compositions described herein have shown efficacy against viral and fungal pathogens.

In addition, although many of the described examples show particular efficacy against respiratory conditions associated with cystic fibrosis, the compositions and methods described herein need not be necessarily limited to a cystic fibrosis application. For example, at least in some embodiments the compositions and methods described herein may be utilized to treat a patient with a respiratory infection even though the patient does not suffer from cystic fibrosis.

Nonionic Metal Nanoparticles

In some embodiments, the metal nanoparticles may comprise or consist essentially of nonionic, ground state metal nanoparticles. Examples include spherical-shaped metal nanoparticles, coral-shaped metal nanoparticles, or a blend of spherical-shaped metal nanoparticles and coral-shaped metal nanoparticles. Preferred embodiments comprise spherical-shaped nanoparticles.

In some embodiments, metal nanoparticles useful for making nanoparticle compositions comprise spherical nanoparticles, preferably spherical-shaped metal nanoparticles having a solid core. The term "spherical-shaped metal nanoparticles" refers to nanoparticles that are made from one or more metals, preferably nonionic, ground state metals, having only internal bond angles and no external edges or bond angles, in contrast to hedron-like, faceted, or crystalline nanoparticles which are often formed using conventional chemical synthesis methods, even though such nanoparticles are often loosely described in the art as being "spherical" in shape.

The nonionic, spherical nanoparticles are highly resistant to ionization, highly stable, and highly resistance to agglomeration. Such nanoparticles can exhibit a high ξ-potential, which permits the spherical nanoparticles to remain dispersed within a polar solvent without a surfactant, even in the absence of a separate anti-agglomeration coating agent, which is a surprising and unexpected result.

In some embodiments, spherical-shaped metal nanoparticles can have a diameter of about 40 nm or less, about 35 nm or less, about 30 nm or less, about 25 nm or less, about 20 nm or less, about 15 nm or less, about 10 nm or less, about 7.5 nm or less, or about 5 nm or less.

In some embodiments, spherical-shaped nanoparticles can have a particle size distribution such that at least 99% of the nanoparticles have a diameter within 30% of the mean diameter of the nanoparticles, or within 20% of the mean diameter, or within 10% of the mean diameter. In some embodiments, spherical-shaped nanoparticles can have a mean particle size and at least 99% of the nanoparticles have a particle size that is within ±3 nm of the mean diameter, ±2 nm of the mean diameter, or ±1 nm of the mean diameter. The mean diameter and/or particle size distribution may be measured using techniques known in the art, such as dynamic light scattering techniques, microscopy techniques (e.g. TEM, SEM) and may be based on either a number or volume distribution.

In some embodiments, spherical-shaped nanoparticles can have a potential (measured as an absolute value) of at least 10 mV, preferably at least about 15 mV, more preferably at least about 20 mV, even more preferably at least about 25 mV, and most preferably at least about 30 mV.

Examples of laser-ablation methods and systems for manufacturing spherical-shaped nanoparticles are disclosed in U.S. Pat. No. 9,849,512 to William Niedermeyer, which is incorporated herein by this reference.

FIGS. 1A-1D show transmission electron microscope (TEM) images of nanoparticles made according to various chemical synthesis methods. As shown, the nanoparticles formed using these various chemical synthesis methods tend to exhibit a clustered, crystalline, faceted, or hedron-like shape rather than a true spherical shape with round and smooth surfaces.

Figure 1B:
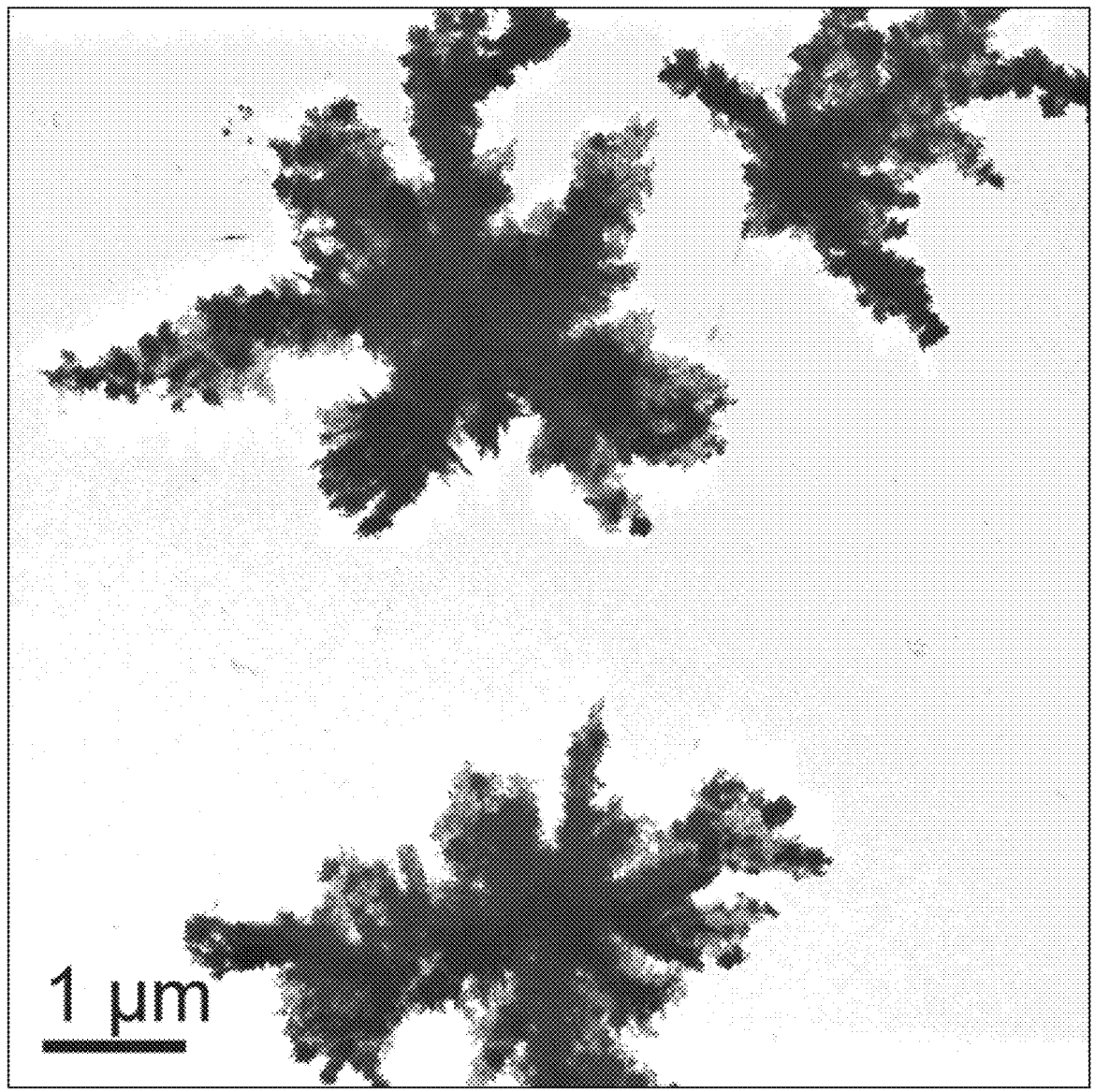
Figure 1C:
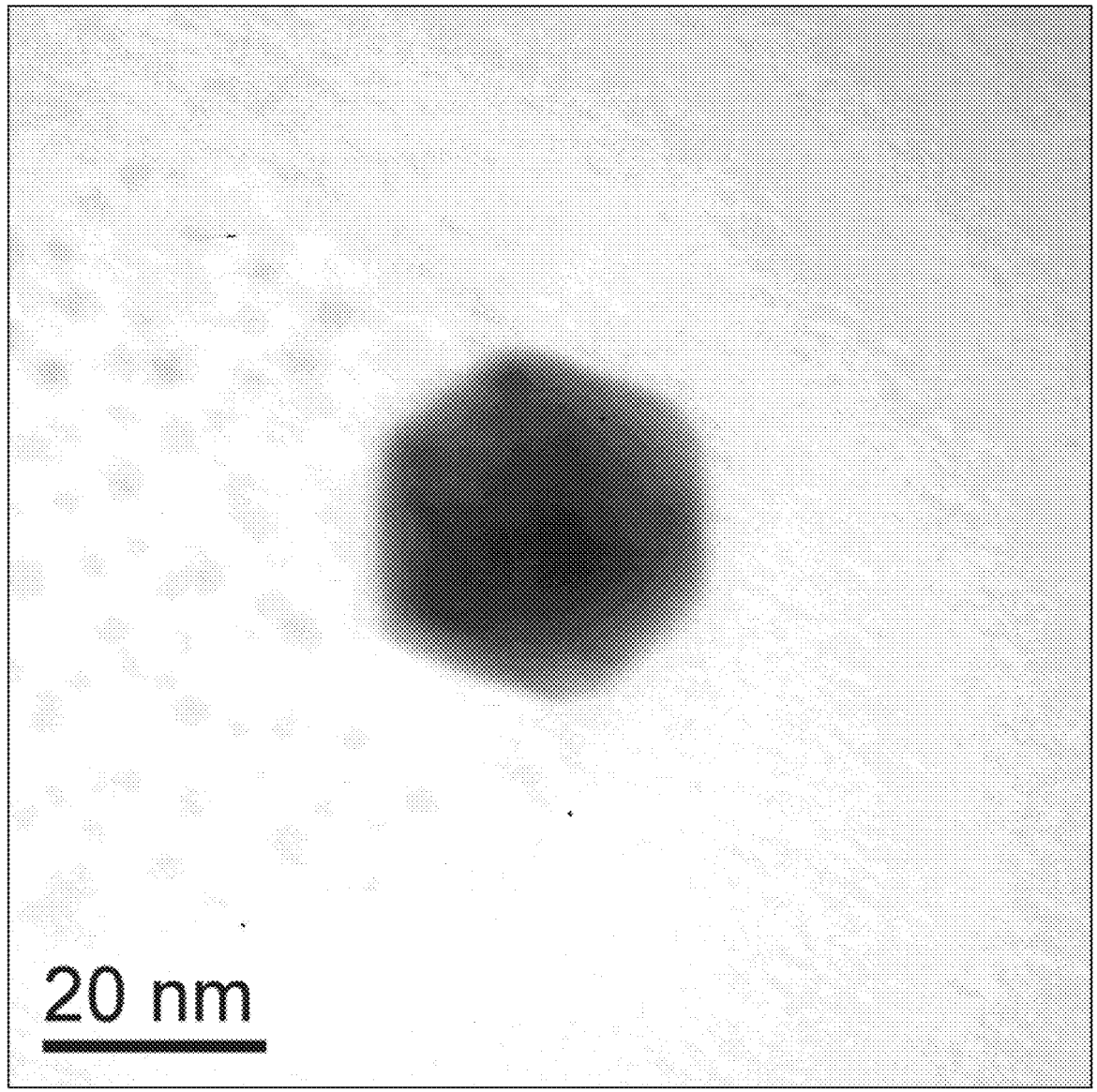
Figure 1D:
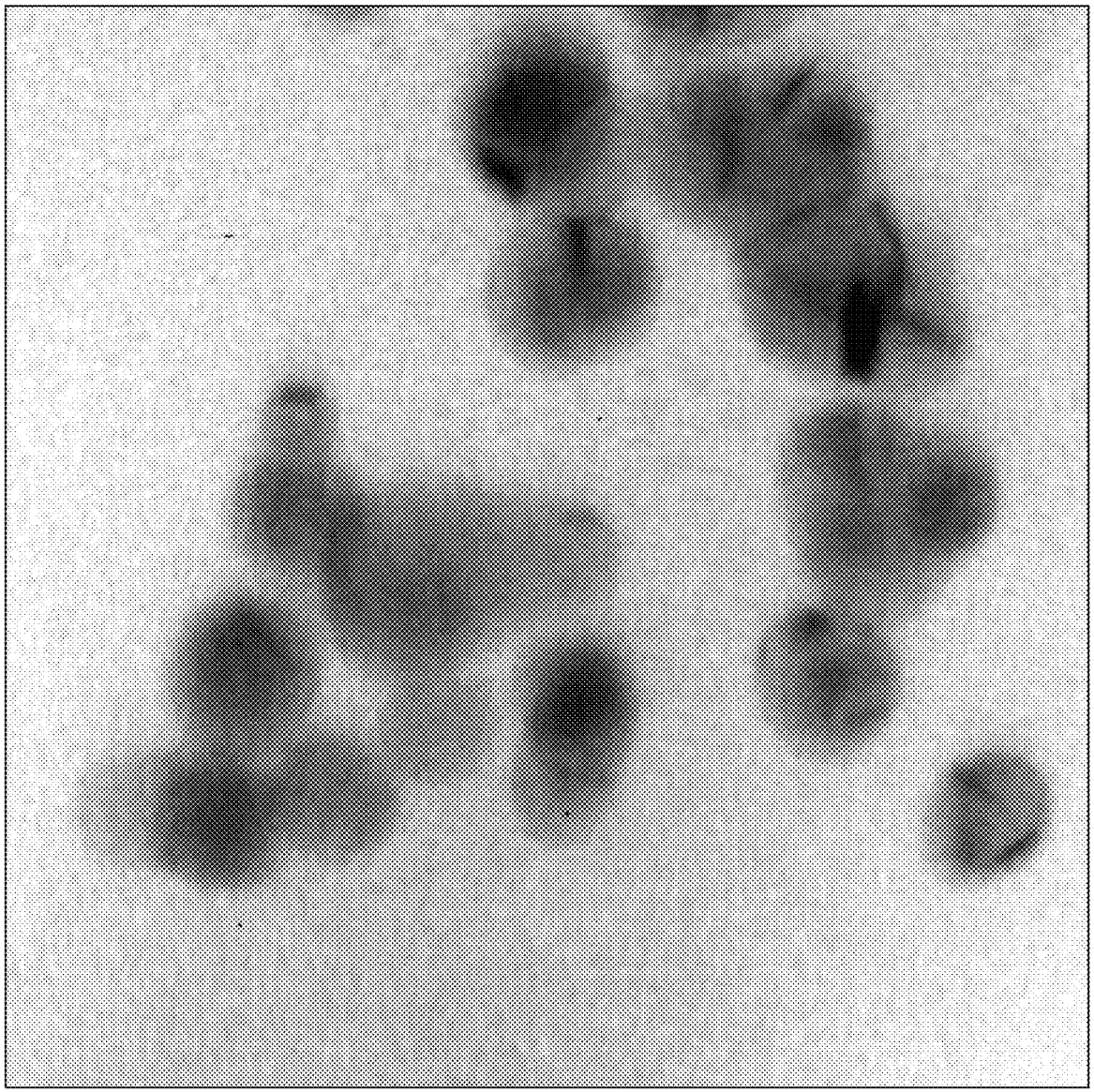

For example, FIG. 1A shows silver nanoparticles formed using a common trisodium citrate method. The nanoparticles are clustered and have a relatively broad size distribution. FIG. 1B shows another set of silver nanoparticles (available from American Biotech Labs, LLC) formed using another chemical synthesis method and showing rough surface morphologies with many edges. FIG. 1C shows a gold nanoparticle having a hedron shape as opposed to a truly spherical shape. FIG. 1D shows a set of silver nanoparticles (sold under the trade name MesoSilver), which have relatively smoother surface morphologies but are understood to be shells of silver formed over a non-metallic seed material.

Figure 2A:
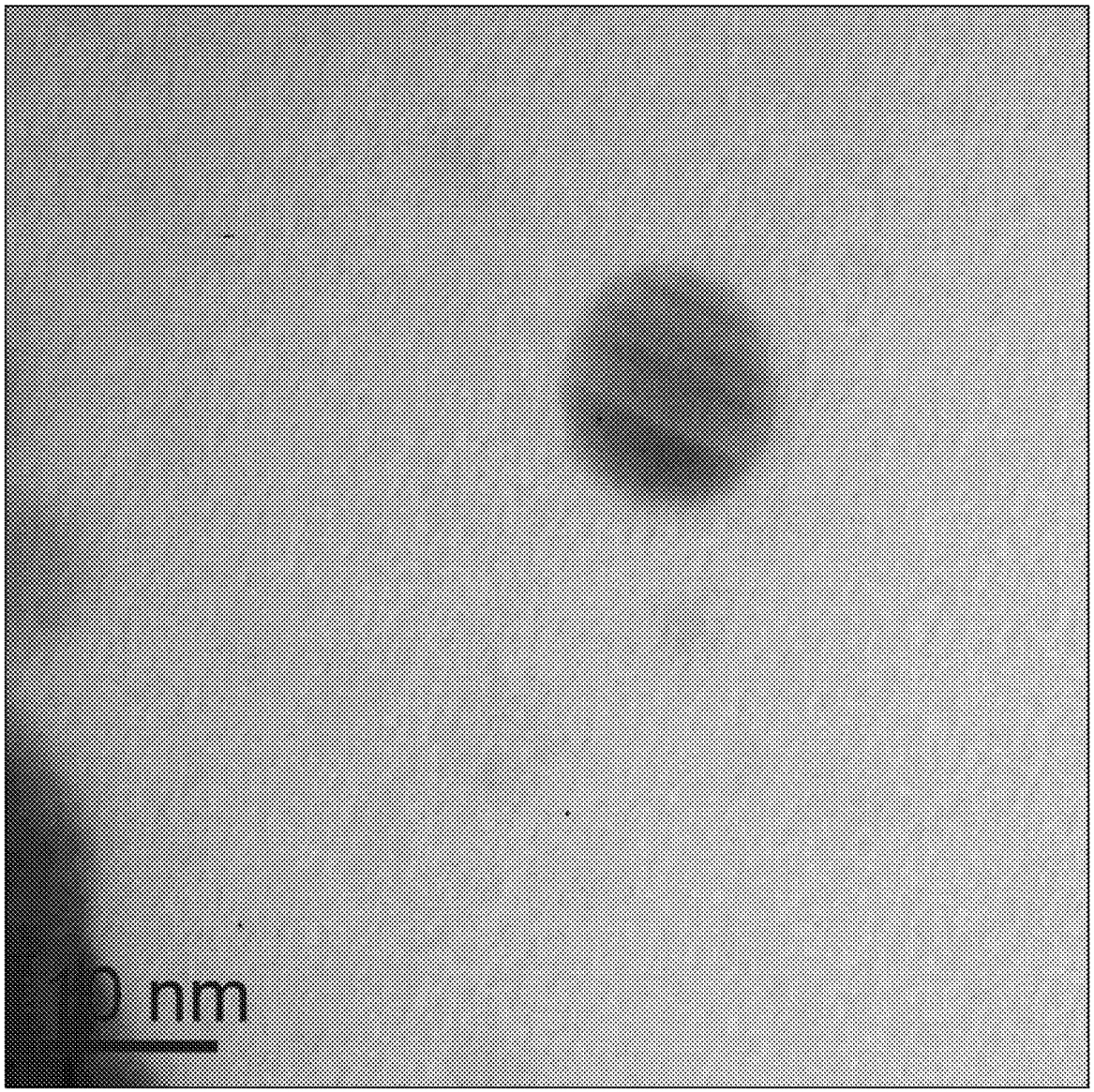
FIGS. 2A-2C show TEM images of exemplary nonionic spherical-shaped metal nanoparticles (i.e., that have no surface edges or external bond angles), the nanoparticles showing substantially uniform size and narrow particle size distribution, smooth surface morphology, and solid metal cores without the use of coating agents.
Figure 2B:
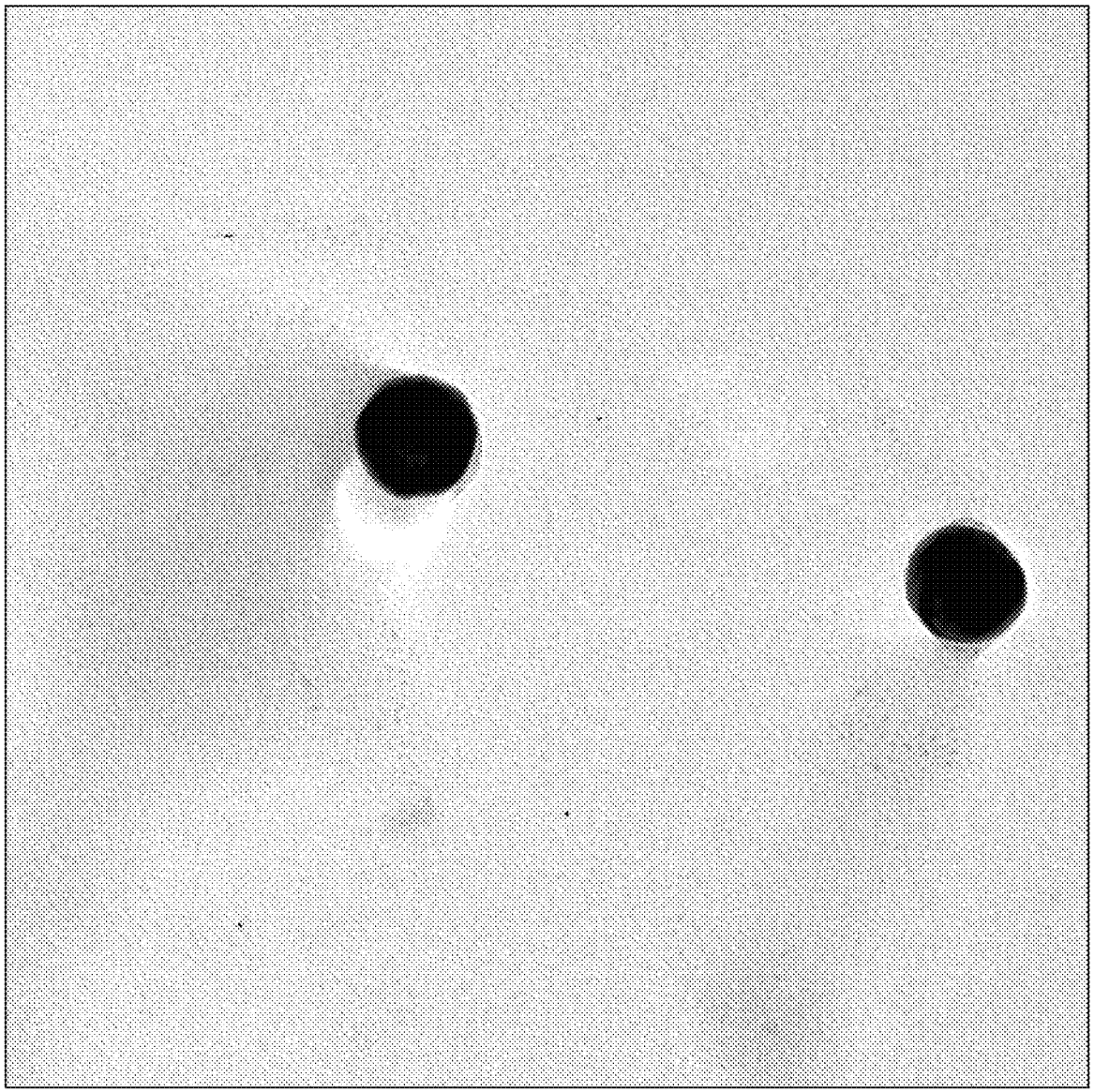
Figure 2C:
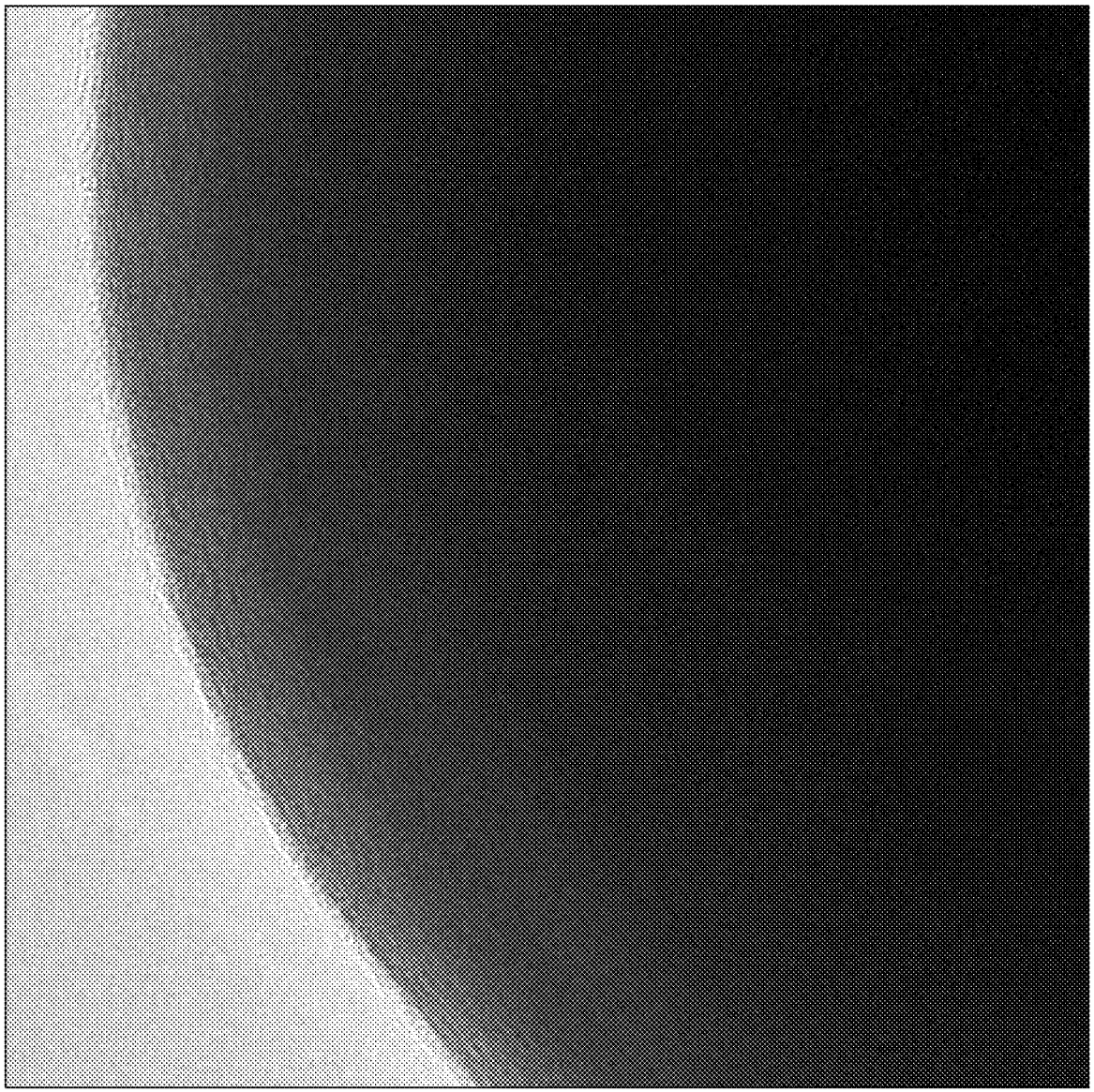

In contrast, the spherical-shaped nanoparticles described herein are solid metal, substantially unclustered, optionally exposed/uncoated, and have a smooth and round surface morphology along with a narrow size distribution. FIGS. 2A-2C show additional TEM images of spherical-shaped nanoparticles. FIG. 2A shows a gold/silver alloy nanoparticle (90% silver and 10% gold by molarity). FIG. 2B shows two spherical nanoparticles side by side to visually illustrate size similarity. FIG. 2C shows a surface of a metal nanoparticle showing the smooth and edgeless surface morphology.

Figure 3A:
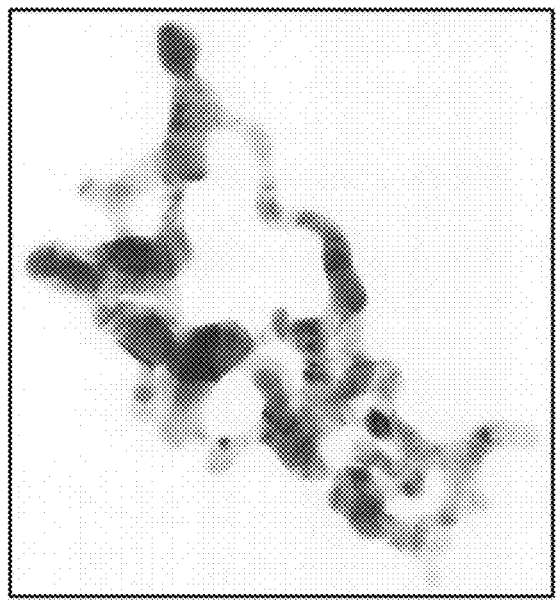
FIGS. 3A-3C show transmission electron microscope (TEM) images of nonionic coral-shaped nanoparticles.
Figure 3B:
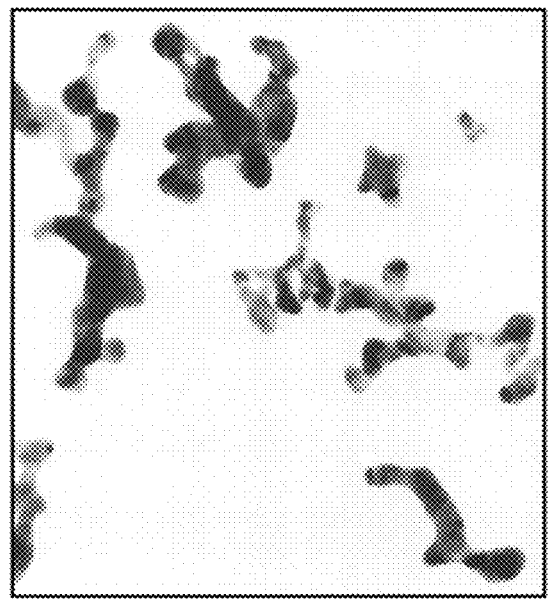
Figure 3C:
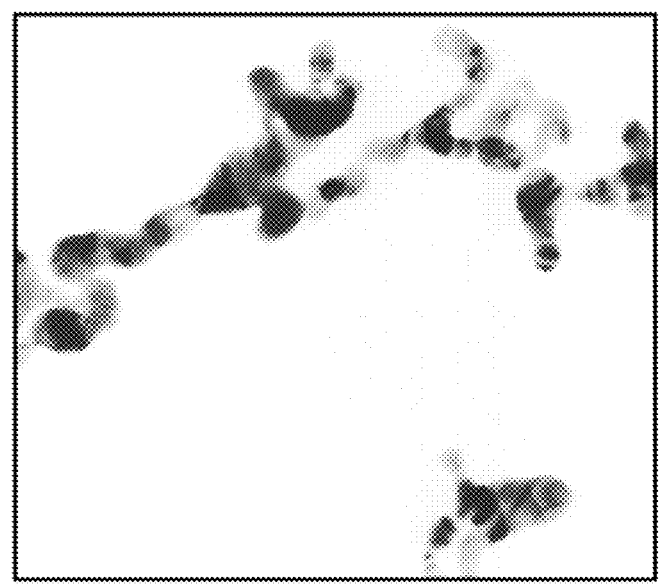

In some embodiments, nonionic metal nanoparticles useful for making nanoparticle compositions may also comprise coral-shaped nanoparticles. The term "coral-shaped metal nanoparticles" refers to nanoparticles that are made from one or more metals, preferably nonionic, ground state metals having a non-uniform cross section and a globular structure formed by multiple, non-linear strands joined together without right angles (see FIGS. 3A-3C). Similar to spherical-shaped nanoparticles, coral-shaped nanoparticles may have only internal bond angles and no external edges or bond angles. In this way, coral-shaped nanoparticles can be highly resistant to ionization, highly stable, and highly resistance to agglomeration. Such coral-shaped nanoparticles can exhibit a high ξ-potential, which permits the coral-shaped nanoparticles to remain dispersed within a polar solvent without a surfactant, which is a surprising and unexpected result.

In some embodiments, coral-shaped nanoparticles can have lengths ranging from about 15 nm to about 100 nm, or about 25 nm to about 95 nm, or about 40 nm to about 90 nm, or about 60 nm to about 85 nm, or about 70 nm to about 80 nm. In some embodiments, coral-shaped nanoparticles can have a particle size distribution such that at least 99% of the nanoparticles have a length within 30% of the mean length, or within 20% of the mean length, or within 10% of the mean length. In some embodiments, coral-shaped nanoparticles can have a ξ-potential of at least 10 mV, preferably at least about 15 mV, more preferably at least about 20 mV, even more preferably at least about 25 mV, and most preferably at least about 30 mV.

Examples of laser-ablation methods and systems for manufacturing coral-shaped nanoparticles are disclosed in U.S. Pat. No. 9,919,363 to William Niedermeyer, which is incorporated herein by this reference.

The metal nanoparticles, including spherical-shaped and/or coral-shaped nanoparticles, may comprise any desired metal, mixture of metals, or metal alloy, including at least one of silver, gold, platinum, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, or alloys thereof. Preferred embodiments comprise silver nanoparticles.

Treatment of Respiratory Infections

The treatment compositions described herein may be used for treating a respiratory infection, and in particular for treating a respiratory infection associated with cystic fibrosis. Beneficially, the nanoparticles may be configured in size and shape to promote effective penetration of mucus in order to reach bacteria within the mucus and in order to reach underlying respiratory tissue.

In some embodiments, the nanoparticles are spherical and have a mean diameter of about 1 nm to about 40 nm, or about 2 nm to about 20 nm, or about 3 nm to about 15 nm, or about 4 nm to about 12 nm, or about 6 nm to about 10 nm, or a size range with endpoints defined by any two of the foregoing values. Nanoparticles within these size ranges, in particular nanoparticles having a mean diameter of about 8 nm, have been found to effectively penetrate mucus while still being capable of effective clearance from the patient's body (e.g., via the lymphatic system and kidneys).

The nanoparticles may be provided in an amount such that when mixed with the carrier, the nanoparticles have a concentration of about 10 ppb to about 100 ppm, or about 50 ppb to about 50 ppm, or about 200 ppb to about 20 ppm, or about 500 ppb to about 10 ppm, or about 1 ppm, or a concentration within a range defined by any two of the foregoing values.

Within these concentration ranges, the nanoparticles have been found to be effective in killing or deactivating targeted microbes. Beneficially, because the nanoparticles are effective even at relatively low concentrations, more dilute doses may be administered (and/or less nanoparticles may be dosed overall), which lowers the clearance burden on the body and reduces the risk of unwanted side-effects such as harm to the patient's own cells/tissues or systemic harm to other beneficial microbiota of the patient.

The carrier may be any pharmaceutically acceptable liquid or solid (e.g., powder) amenable to administration via inhalation. In one embodiment, the carrier comprises a saline solution. The carrier may optionally include one or more excipients suitable for use in an inhalation application. Suitable excipients include, for example, inhalable bulking powders, carbohydrates such as monosaccharides (e.g., glucose, arabinose), disaccharides (e.g., lactose, saccharose, maltose), and oligo- and polysaccharides (e.g., dextran, cyclodextrins), alcohols and polyalcohols (e.g., ethanol, sorbitol, mannitol, xylitol), salts (e.g., sodium chloride, calcium carbonate, carboxylic acid salts, fatty acid salts), amino acids (e.g., glycine), buffers (e.g., citrate, phosphate, acetate), or combinations thereof.

The treatment composition may be administered using any suitable inhalation route, including through the use of a metered-dose inhaler, a nebulizer, and/or a dry powder dispersion device. These types of devices typically include a mouthpiece or facemask enabling transfer of nebulized/atomized medicament to the patient. A nebulizer may be an ultrasonic nebulizer, a jet nebulizer, a vibrating mesh nebulizer, or a soft mist inhaler, for example.

The treatment compositions have shown versatile efficacy in treating a wide variety of bacteria, including several problematic bacterial strains that have resistance to one or more conventional antibiotics. In some embodiments, the respiratory infection may be associated with one or more of: *Staphylococcus aureus* (e.g., including methicillin-resistant *Staphylococcus aureus*), *Escherichia coli, Listeria, Salmonella, Pseudomonas* (e.g., including mucoid and non-mucoid *Pseudomonas* and/or meropenem-resistant *Pseudomonas*), nontuberculosis mycobacteria (e.g., including *Mycobacterium abscessus* complex and *Mycobacterium avium* complex), *Acinetobacter, Strenotrophomonas* (e.g., *Strenotrophomonas maltophilia*), *Achromobacter*, and *Burkholderia cepacia* complex (e.g., including one or more of *Burkholderia cenocepacia, Burkholderia multivorans*, and *Burkholderia dolosa*), for example.

The treatment compositions have also shown efficacy in treating various pathogenic fungi sometimes associated with respiratory infections. In some embodiments, a respiratory infection may by associated with one or more of *Aspergillus* (e.g., *Aspergillus niger*), *Fusarium* (e.g., *Fusarium solani* complex), *Coccidioides, Histoplasma, Pneumocystis* (e.g., *Pneumocystis jirovecii*), *Cryptococcus* (e.g., *Cryptococcus neoformans, Cryptococcus gatti*), *Candida* (e.g., *Candida albicans*), and *Blastomyces*, for example.

The treatment composition may also have efficacy in killing or deactivating viruses sometimes associated with respiratory infections, such as influenza virus, rhinovirus, respiratory syncytial virus (RSV), parainfluenza virus, adenoviruses, herpes, and rotavirus, for example.

Antimicrobial Activity

Figure 4A:
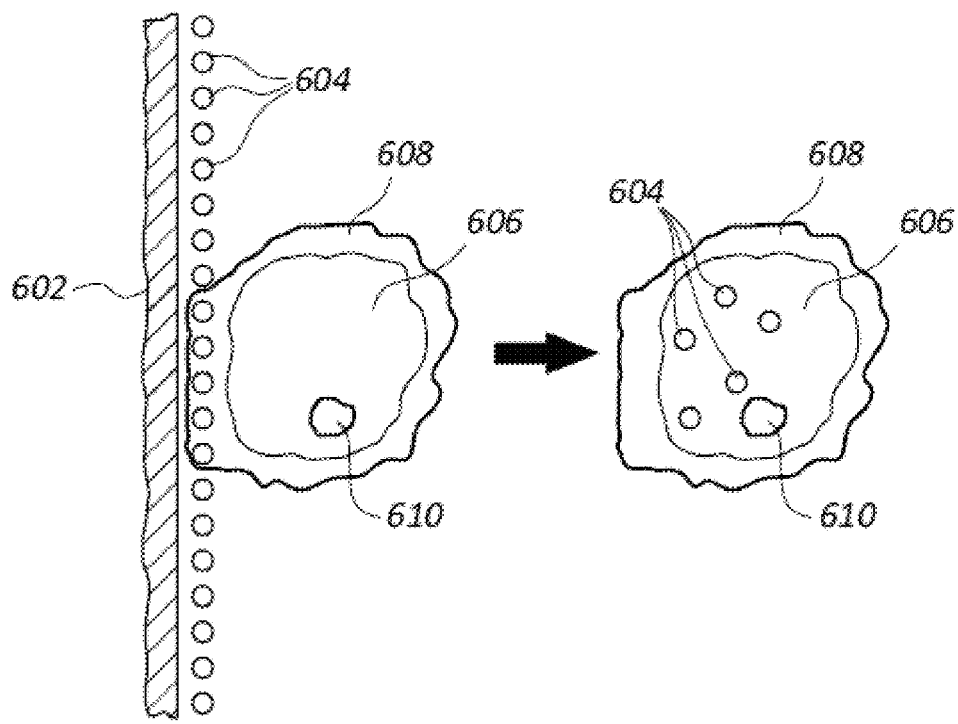
FIGS. 4A-4C schematically illustrated a proposed mechanism of action by which the nanoparticles can kill or deactivate bacteria.

FIG. 4A schematically illustrates a bacterium 608 having absorbed spherical-shaped nanoparticles 604 from a substrate 602 (e.g., from a mucus layer), such as by active absorption or other transport mechanism. The nanoparticles 604 can freely move throughout the interior 606 of bacterium 608 and come into contact with one or more vital proteins or enzymes 610 that, if denatured, will kill or disable the bacterium. A similar mechanism may function where viral or fungal pathogens are involved. Unlike most conventional antibiotics, the nanoparticles effectively kill or deactivate the bacterium without significantly disrupting the cell wall and therefore without significant lysing of the bacteria coming into contact with the nanoparticles.

Figure 4B:
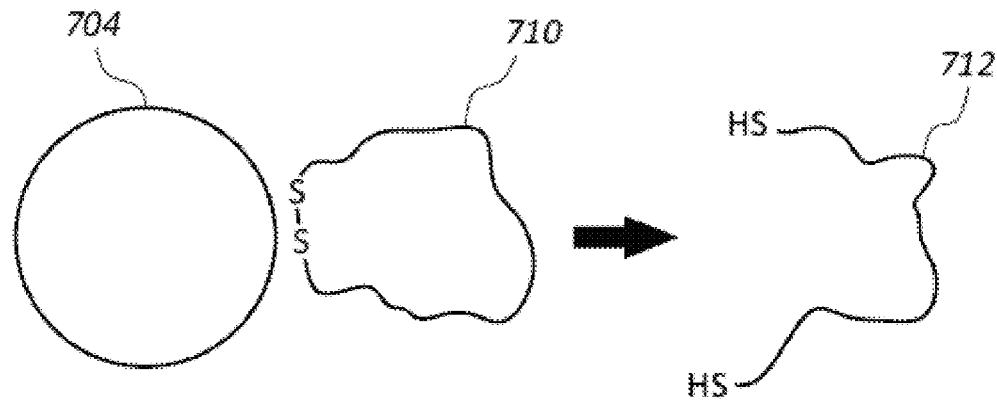

For example, one way that nanoparticles may kill or denature a microbe is by catalyzing the cleavage of disulfide (S—S) bonds within a vital protein or enzyme. FIG. 4B schematically illustrates a microbe protein or enzyme 710 with disulfide bonds being catalytically denatured by an adjacent spherical-shaped nanoparticle 704 to yield denatured protein or enzyme 712. In the case of bacteria or fungi, the cleavage of disulfide bonds and/or cleavage of other chemical bonds of vital proteins or enzymes may occur within the cell interior and thereby function to kill the microbe in this manner without causing significant lysis. Such catalytic cleavage of disulfide (S—S) bonds is facilitated by the generally simple protein structures of microbes, in which many vital disulfide bonds are on exposed and readily cleaved by catalysis.

Another potential mechanism by which metal (e.g., silver) nanoparticles can kill microbes is through the production of active oxygen species, such as peroxides, which can oxidatively cleave protein bonds, including but not limited to amide bonds.

Figure 4C:
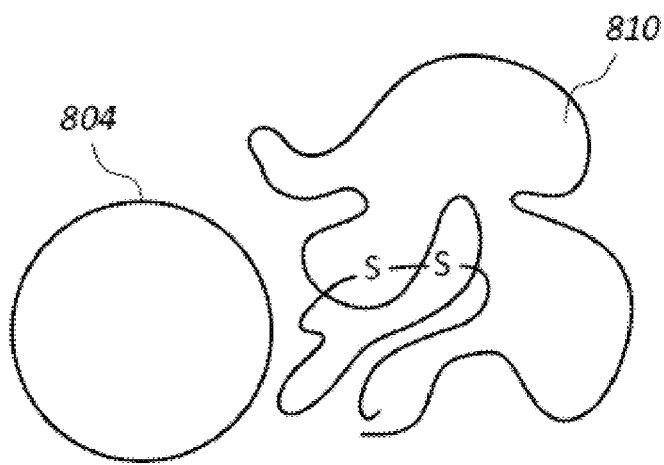

Notwithstanding the lethal nature of nonionic metal nanoparticles relative to microbes, they can be relatively harmless to humans, mammals, and healthy mammalian cells, which contain much more complex protein structures compared to simple microbes in which most or all vital disulfide bonds are shielded by other, more stable regions of the protein. FIG. 4C schematically illustrates a mammalian protein 810 with disulfide (S—S) bonds that are shielded so as to resist being catalytically denatured by an adjacent spherical-shaped nanoparticle 804. In many cases the nonionic nanoparticles do not interact with or attach to human or mammalian cells and can be quickly and safely expelled through the urine without damaging kidneys or other cells, tissues, or organs.

The metal nanoparticles kill bacteria without significant release of silver (Ag+) or other metal ions. Because the metal nanoparticles do not release significant quantities of silver or other metal ions, they are essentially non-toxic to humans and other animals (i.e., whatever amount or concentration of ions, if any, that are released from the metal nanoparticles is/are below a threshold toxicity level at which they become toxic to humans, other mammals, birds, reptiles, fish, and amphibians).

In the particular case of silver (Ag) nanoparticles, the interaction of the silver (Ag) nanoparticle(s) within a microbe has been demonstrated to be particularly lethal without the need to rely on the production of silver ions (Ag$^+$) to provide the desired antimicrobial effects, as is typically the case with conventional colloidal silver compositions. The ability of silver (Ag) nanoparticles to provide effective microbial control without any significant or actual release of toxic silver ions (Ag$^+$) into the patient or the surrounding environment is a substantial advancement in the art. Whatever amount or concentration of silver ions released by silver nanoparticles, if any, is well below known or inherent toxicity levels for animals, such as mammals, birds, reptiles, fish, and amphibians.

As used herein, the modifying term "significant" means that the effect the term is modifying is clinically noticeable and relevant. Thus, the phrase "without significant release of silver ions" means that though there may technically be some small amount of detectable ion release, the amount is so small as to be clinically and functionally negligible. Similarly, the phrase "without significant cell lysis" means that although there may be some observable cell lysis, the amount is negligible and only tangentially related to the actual primary mechanism of cell death/deactivation.

EXAMPLES

In the following examples, the nonionic, ground state, uncoated metal nanoparticles described above may be referred to as "Attostat" nanoparticles, "Niedermeyer" nanoparticles, "Attostat Ag," or the like. Except where noted otherwise, the Attostat nanoparticles utilized were spherical, silver nanoparticles having a size of about 4 nm to about 12 nm, or more typically about 6 nm to about 10 nm.

Example 1

Testing measured the transepithelial electrical resistance (TER) of a nanoparticle composition applied to the apical surface of cystic fibrosis patient derived primary cultures of bronchial epithelia (maintained in ALI cultures). TER is a measure of epithelial tight junction integrity which underlies the physical barrier function of airway epithelia. Changes in TER of 12 epithelia were observed over 24 hours.

Changes in measured TER of epithelia treated with spherical, nonionic, ground state silver nanoparticle formulations at 3 ppm were not significantly different from the responses to vehicle treatment at the sampled time points, as determined with ANOVA and Turkey-Kramer HSD post-test analysis with P<0.05. The impact of the silver nanoparticle formulations on the barrier function of well differentiated primary CF bronchial epithelia was therefore not distinct from the impact of vehicle treatment.

Further, there were no visually distinct differences in microscopic appearance of the epithelia at about 100× magnification in a phase contrast microscope. Ciliary activity was also similar across treatment groups. These results were surprising given the general belief that silver nanoparticles of such size would release silver ions and be toxic to such cells.

Example 2

This test compared the effect on zebra fish of nonionic, ground state silver nanoparticles formed via laser ablation compared to other silver nanoparticles formed through conventional chemical synthesis or electrolysis methods, silver nitrate, and a control tank with plain water. The nanoparticles formed through a chemical synthesis process and the nanoparticles formed through an electrolysis process both caused the fish to exhibit signs of toxicity, including death, slowed movement and settling near the bottom of the tank. The nanoparticles formed through an electrolysis process and the silver nitrate both killed the fish within 2 hours of exposure.

In contrast, the fish in the tank treated with the nonionic, ground state silver nanoparticles of the present application and the fish in the control tank were equally healthy and active. None of the zebrafish exposed to the nonionic, ground state silver nanoparticles of the present application died during the course of the study, whereas all other treatments were associated with at least some zebrafish death.

The results of the zebrafish study were surprising in light of the general knowledge that silver nanoparticles show toxicity in such studies. For example, the authors of Mansouri et al., "Effects of Short-Term Exposure to Sublethal Concentrations of Silver Nanoparticles on Histopathology and Electron Microscope Ultrastructure of Zebrafish (*Danio*

Rerio) Gills," *Iranian J. Toxicity*, Vol. 10, No 1, January-February 2016, state the concern that "[t]he increasing use of nanomaterials and nanoproducts has increased the possibility of contamination of the environment, which may have adverse effects on different organisms" (Abstract). The authors concluded, following the study, that "[b]ased on the adverse effects of AgNPs [silver nanoparticles] on zebrafish gills, silver nanoparticle solutions can be hazardous pollutants for the environment" (page 15).

Example 3

Neutrophil testing was done using complete blood count (CBC) analysis. Testing 0.2 and 1.0 µg/mL (i.e., ppm) of Attostat Ag showed that after up to 6 hours exposure time, no blood panel values deviated from normal ranges. At 24 hours exposure time, both control and test samples showed borderline values for MCHC (Mean Corpuscular Hemoglobin Concentration, just below minimum normal range) and MPV (Mean Platelet Volume, just above the maximum normal range).

The only deviation from normal values occurred in the 0.2 µg/mL Attostat Ag sample, which exhibited very slight elevation in EOS % (Eosinophil Percentage, just above maximum normal range). Overall, these results show no significant toxicological effects on the full spectrum of blood cells and components. This is particularly encouraging as forecasted therapeutics typically would not exceed 8-10 µg/mL, resulting in much lower local concentrations throughout the bloodstream and other portions of the body.

Example 4

Antimicrobial efficacy tests were performed using 0.5 µg/mL Attostat Ag against five common bacterial strains associated with respiratory infections of cystic fibrosis patients:
  *Staphylococcus aureus*
  MRSA
  *E. coli*
  *Listeria*
  *Salmonella*

Staph and MRSA both had >99% kill within 24 hours. *E. coli*, *Listeria*, and *Salmonella* both had >99% kill in approximately 12 hours.

Example 5

A certified Tobramycin resistant strain of *Pseudomonas aeruginosa* was acquired from the University of Michigan and subjected to GLP Time Kill Studies. At an 0.8 µg/mL overall exposure level of Attostat Ag, the study yielded results proving high efficacy, >99%, within 1 hour of exposure.

Example 6

Following successful results against tobramycin-resistant *Pseudomonas*, similar testing with *B. cepacia* complex (BCC) was performed. Samples of two of the most widespread strains, *Burkholderia cenocepacia* and *Burkholderia multivorans*, were obtained. Cultures of these BCC species were subjected to GLP Time Kill Studies. Attostat Ag proved highly effective against the strains with >99% kill within 1 hour of exposure for *B. cenocepacia* and >97% kill for *B. multivorans* within 1 hour of exposure (0.8 µg/mL exposure level).

Example 7

Efficacy tests similar to those of Examples 5 and 6 were performed to compare the efficacy of Attostat Ag to tobramycin. Testing showed equal colony reduction using 4 µg/mL Attostat Ag vs 20 µg/mL tobramycin. Increasing Attostat Ag concentration to 6 µg/mL had greater colony reduction to 20 µg/mL tobramycin. Table 1 summarizes testing results from Examples 4 through 7.

TABLE 1

| Organism | Exposure (hours) | Average Control Titer (CFU/ml) | Average Test Titer (CFU/ml) | Percent Reduction (%) | $Log_{10}$ Reduction |
|---|---|---|---|---|---|
| *Staphylococcus aureus* | 6 | $4.8 \times 10^6$ | $1.5 \times 10^6$ | 68 | 0.49 |
|  | 12 |  | $3.7 \times 10^4$ | 99.23 | 2.11 |
|  | 24 |  | $9.9 \times 10^2$ | 99.979 | 3.68 |
| Methicillin Resistant *S. aureus* (MRSA) | 6 | $5.3 \times 10^6$ | $4.4 \times 10^6$ | 17 | 0.08 |
|  | 12 |  | $1.2 \times 10^4$ | 78 | 0.66 |
|  | 24 |  | $1.1 \times 10^4$ | 99.8 | 2.7 |
| *Escherichia coli* | 6 | $9.5 \times 10^6$ | $1.5 \times 10^6$ | 84 | 0.79 |
|  | 12 |  | $1.3 \times 10^4$ | 99.86 | 2.86 |
|  | 24 |  | $<2.0 \times 10^1$ | 99.999 | >5.86 |
| *Listeria monocytogenes* | 6 | $7.0 \times 10^7$ | $~1.0 \times 10^7$ | ~86 | ~0.84 |
|  | 12 |  | $2.7 \times 10^6$ | 96.2 | 1.42 |
|  | 24 |  | $9.1 \times 10^3$ | 99.987 | 3.88 |
| *Salmonella enterica* | 6 | $2.9 \times 10^7$ | $1.5 \times 10^4$ | 99.949 | 3.29 |
|  | 12 |  | $~8.0 \times 10^1$ | ~99.999 | ~5.56 |
|  | 24 |  | $<2.0 \times 10^1$ | >99.999 | >6.16 |
| Tobramycin Resistant *P. aeruginosa* | Control: 1 | $2.0 \times 10^6$ | $1.7 \times 10^6$ | 15 | 0.07 |
|  | 1 |  | $3.3 \times 10^1$ | 99.999 | 4.78 |
|  | 6 |  | $<2.0 \times 10^1$ | >99.999 | >5.00 |
|  | 12 |  | $<2.0 \times 10^1$ | >99.999 | >5.00 |
|  | 24 |  | $<2.0 \times 10^1$ | >99.999 | >5.00 |
| *Burkholderia cenocepacia* | Control: 1 | $3.9 \times 10^6$ | $2.1 \times 10^6$ | 47 | 0.27 |
|  | 1 |  | $1.3 \times 10^3$ | 99.97 | 3.46 |
|  | 6 |  | $~4.8 \times 10^2$ | ~99.988 | ~3.91 |
|  | 12 |  | $~8.7 \times 10^1$ | ~99.998 | ~4.65 |
|  | 24 |  | $~2.3 \times 10^1$ | ~99.999 | ~5.22 |
| *Burkholderia multivorans* | Control: 1 | $2.5 \times 10^6$ | $1.9 \times 10^8$ | 25 | 0.13 |
|  | 1 |  | $6.2 \times 10^6$ | 97.5 | 1.61 |
|  | 6 |  | $~1.8 \times 10^3$ | ~99.999 | ~5.14 |
|  | 12 |  | $~3.0 \times 10^1$ | ~99.999 | ~6.93 |
|  | 24 |  | $~2.0 \times 10^1$ | ~99.999 | ~7.10 |

Example 8

Sputum testing was also performed using sputum donated by two individuals diagnosed with cystic fibrosis. Both patients suffer from tobramycin-resistant *Pseudomonas*. Initial antimicrobial efficacy testing involved culturing sputum samples in Buffered Peptone Water (BPW) overnight at various dilutions. Cultures were then used to dose well plates with anywhere from 0-10 µg/mL Attostat Ag. After 24 hours, samples treated with Attostat Ag exhibited 95-99+% bacterial kill in all cases.

Example 9

An immunocompromised cancer patient undergoing chemotherapy and radiation therapy contracted a *Fusarium* fungal infection of the nasal cavity. Under the care of the supervising physician, the patient was treated with Attostat Ag via nasal inhaler. The *Fusarium* infection was cured following treatment.

Example 10

Lyophilized quality control organisms were re-hydrated and grown for isolation on agar plates as indicated by the supplier in Tryptic Soy Broth or other appropriate medium and incubated. If needed, the resulting suspension was diluted in an appropriate medium so as the final concentration of the organism in the product being challenged falls between $1.0 \times 10^5$ and $1.0 \times 10^6$.

The product was partitioned in to 20 g aliquots in to which 100 µl of test organism was added to yield a target concentration of $\sim 5.0 \times 10^5$ organisms per mL of product. After thoroughly mixed, each sample cup was allowed to sit for the time intervals indicated in the attached report, at which point 1.0 g aliquots were taken and diluted 1:10, with further dilutions performed as necessary. Each tube was thoroughly vortexed. From each dilution, 1 mL aliquots of solution were removed and plated on to Tryptic Soy Agar plates (or other appropriate media), and then incubated under the conditions appropriate for each test organism. Following the appropriate incubation period, colony counts were taken and reported.

Log reduction values were calculated as: Log Reduction=$\log_{10}(A/B)$, where A is the number of viable microorganisms before treatment and B is the number of viable microorganisms after treatment and time interval. Where no colonies were observed on the plates, results of less than (<) the minimum detection limit (ie. <10 cfu's/g) were reported. In these cases, the log reduction was calculated based on the minimum detection limit and reported as a greater than value. Results are summarized in Table 2.

TABLE 2

| Organism | Initial | Day 1 | Day 3 | Day 1 Log Reduction | Day 3 Log Reduction |
|---|---|---|---|---|---|
| Aspergillus niger ATCC 16404 | $1.5 \times 10^5$ | 500 | 150 | 2.48 | 3.00 |
| Penicillium rubens ATCC 9179 | $4.0 \times 10^5$ | 400 | 350 | 3.00 | 3.06 |

Example 11

Figure 5:
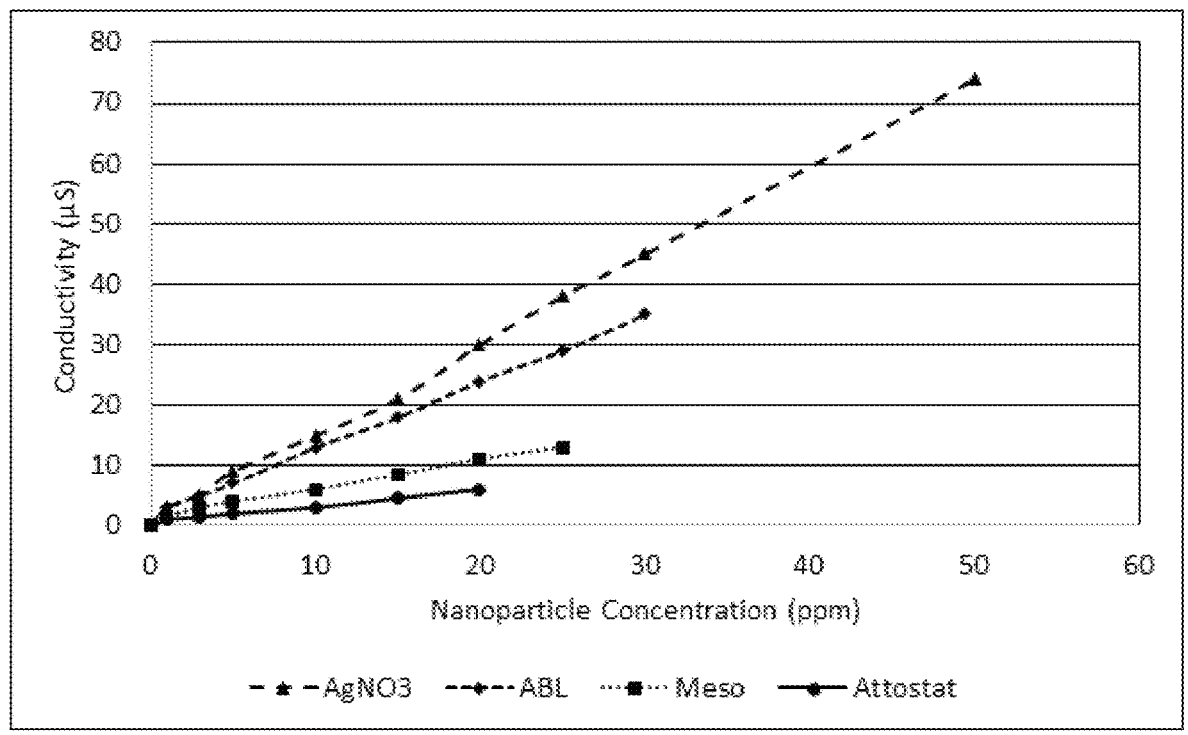
FIG. 5 illustrates the results of conductivity testing comparing various nanoparticle solutions and showing that spherical, metal nanoparticles according to the disclosed embodiments are nonionic.

FIG. 5 illustrates the results of conductivity testing comparing various nanoparticle solutions. In Exhibit A, "Attostat" corresponds to spherical-shaped, nonionic silver nanoparticles formed by laser ablation such as described herein, "AgNO$_3$" is silver nitrate, "Meso" represents a commercially available silver nanoparticle formulation with nanoparticles formed through a chemical reduction process, and "ABL" represents a commercially available silver nanoparticle formulation understood to be formed through an electrolysis process.

The results illustrate that the Attostat nanoparticle formulation had significantly less ion release than any of the other tested nanoparticle formulations. It should be noted that the measured conductivity for Attostat nanoparticle formulations, even at the highest measured concentration of 16 ppm, remained low enough to be on par with typical conductivity measurements for high quality deionized water.

Example 12

An antibacterial efficacy test was carried out comparing a "Niedermeyer" nanoparticle formulation (8 nm size) against silver nitrate and against the National Institute of Standards and Technology (NIST) Standard Nanocomposix 10 nm silver nanoparticles. The NIST nanoparticles are formed by a chemical reduction process that utilizes citrate as reducing and capping agent. The NIST nanoparticles have a conductivity similar to the "Meso" nanoparticles of Example 11, with detectable but low levels of silver ions.

Relative Light Unit (RLU) counts were recorded at 12 hours and 24 hours post treatment. RLU measurements were carried out using a Hygiena SystemSURE Plus V.2 SN067503 RLU meter with Hygenia AquaSnap TOTAL ATP Water Test Cat #U143 Lot #153019. Culturing media was Hardy Diagnostics Buffered Peptone Water Lot #118272. Samples were prepared with the nanoparticle treatments and then diluted with the media to provide the tested concentrations. The test organism (Microbiologics, *E. coli*, KwikStik, ATCC #51813, Ref #0791 K, Lot #791-1-6) was incubated in fresh Buffered Peptone Water growth media for 24 hours prior to exposure to the nanoparticle treatments. Tables 3 and 4 illustrate results of RLU counts 12 and 24 hours post nanoparticle treatment, respectively.

TABLE 3

RLU Counts at 12 Hours Post Exposure to Nanoparticle Treatment

| Concentration | Attostat 8 nm Particles | NIST Standard Particles 10 nm | AgNO3 Silver Nitrate |
|---|---|---|---|
| Control 0 ppm (mg/L) | 6256 | 7037 | 6731 |
| 0.25 ppm (mg/L) | 65 | 6908 | 80 |
| 0.5 ppm (mg/L) | 72 | 5416 | 75 |
| 1.0 ppm (mg/L) | 30 | 7189 | 84 |

TABLE 4

RLU Counts at 24 Hours Post Exposure to Nanoparticle Treatment

| Concentration | Attostat 8 nm Particles | NIST Standard Particles 10 nm | AgNO3 Silver Nitrate |
|---|---|---|---|
| Control 0 ppm (mg/L) | 7595 | 5421 | 7342 |
| 0.25 ppm (mg/L) | 25 | 5691 | 25 |
| 0.5 ppm (mg/L) | 8 | 3950 | 46 |
| 1.0 ppm (mg/L) | 30 | 3834 | 30 |

Tables 5 and 6 represent the data in terms of comparing each treatment to its respective control at 12 and 24 hours post treatment, respectively.

TABLE 5

RLU as percentage of control at 12 Hours Post Treatment

| Concentration | Attostat 8 nm Particles | NIST Standard Particles 10 nm | AgNO3 Silver Nitrate |
|---|---|---|---|
| Control 0 ppm (mg/L) | 100% | 100% | 100% |
| 0.25 ppm (mg/L) | 1.0% | 98.2% | 1.2% |
| 0.5 ppm (mg/L) | 1.1% | 77.0% | 1.1% |
| 1.0 ppm (mg/L) | 0.6% | 102.2% | 1.3% |

TABLE 6

RLU as percentage of control at 24 Hours Post Treatment

| Concentration | Attostat 8 nm Particles | NIST Standard Particles 10 nm | AgNO3 Silver Nitrate |
|---|---|---|---|
| Control 0 ppm (mg/L) | 100% | 100% | 100% |
| 0.25 ppm (mg/L) | 0.33% | 105% | 0.34% |
| 0.5 ppm (mg/L) | 0.11% | 72.9% | 0.62% |
| 1.0 ppm (mg/L) | 0.39% | 70.7% | 0.41% |

As shown, at all concentrations tested, the Attostat nanoparticles reduced the number of RLU counts to less than 1.5% from the control baseline at both the 12 hour and 24 hour measurement periods. Anything below 1.5% is below level of accurate detection and is considered a complete kill.

The Attostat nanoparticles effectively reduced RLU counts to below the 1.5% threshold at all tested concentrations. The NIST nanoparticles appeared to show a trend toward greater efficacy at higher concentrations, which would correspond to a normal diffusion model, but even at the highest tested concentration still only reached an RLU count of 70.7% of the initial control baseline at the 24 hour measurement.

The low antimicrobial efficacy of the NIST nanoparticles at the concentrations tested as compared to the silver nitrate could potentially be explained by the lower conductivity, and thus lower ion concentration, of the NIST nanoparticles as compared to the silver nitrate. However, the significant efficacy of the Attostat nanoparticles was surprising given the fact that the Attostat nanoparticles have significantly low to non-detectable levels of ions, even lower than the NIST particles. The Attostat nanoparticles continued to provide antimicrobial activity through the 24 hour testing period with no signs of reduced efficacy.

The invention claimed is:

1. A method for treating a bacterial respiratory infection in a patient with cystic fibrosis and a thick mucus layer in the patient's lungs caused by cystic fibrosis, the method comprising:
   administering a treatment composition to the patient with cystic fibrosis via inhalation into the patient's lungs, wherein the patient's lungs contain a thick viscous mucus layer caused by cystic fibrosis and the bacterial respiratory infection is caused by one or more bacteria selected from *Escherichia coli, Listeria, Salmonella, Pseudomonas*, nontuberculosis mycobacteria, *Acinelobacler, Sirenolrophomonas maltophilia, Achromobacter, tobramycin*-resistant *Pseudomonas*, multidrug-resistant *Pseudomonas aeruginosa*, or *Burkholderia cepacia* complex, with the proviso that the bacterial respiratory infection is not caused by methicillin-resistant *Staphylococcus aureus* or *Pneumocyslis*, wherein the bacteria causing the bacterial respiratory infection are located in both the thick viscous mucus layer and in infected respiratory tissue, and wherein the treatment composition comprises:
      nonionic, ground state, spherical silver nanoparticles having a mean diameter in a range of about 1 nm to about 20 nm and a particle size distribution such that at least 99% of the silver nanoparticles have a diameter within 30% of the mean diameter, wherein the nanoparticles are non-crystalline with no external edges or bond angles and are uncoated, and
      a carrier formulated for administration via inhalation, and
   the treatment composition treating the bacterial respiratory infection by the silver nanoparticles penetrating the thick viscous mucus layer, reaching the infected respiratory tissue, and killing the bacteria causing the bacterial respiratory infection in both the thick viscous mucus layer and the infected respiratory tissue without the release of silver ions.

2. The method of claim 1, wherein the silver nanoparticles effectively kill multiple types of bacteria residing within the thick viscous mucus layer and the infected respiratory tissue without the release of silver ions.

3. The method of claim 1, wherein the treatment composition is administered to the patient via inhalation using a metered-dose inhaler.

4. The method of claim 1, wherein the treatment composition is administered to the patient via inhalation using a nebulizer.

5. The method of claim 1, wherein the bacterial respiratory infection comprises an infection with two or more of *Escherichia coli, Listeria, Salmonella, Pseudomonas*, nontuberculosis mycobacteria, *Acinetobacter, Strenotrophomonas mallophilia, Achromobacter*, or *Burkholaderia cepacia* complex.

6. The method of claim 1, wherein the bacterial respiratory infection comprises an infection with two or more of tobbramycin-resistant *Pseudomonas*, multidrug-resistant *Pseudomonas aeruginosa, Strenotrophomonas mallophilia*, or *Burkholderia cepacia* complex.

7. The method of claim 1, wherein the bacterial respiratory infection comprises an infection with one or more antibiotic resistant bacteria.

8. The method of claim 1, wherein the nanoparticles kill the one or more bacteria without lysing the bacteria.

9. The method of claim 1, wherein the nanoparticles kill the one or more bacteria without damaging lung epithelia.

10. The method of claim 1, wherein the nonionic, ground state, spherical silver nanoparticles have a mean diameter of about 3 nm to about 15 nm.

11. The method of claim 1, wherein the carrier comprises saline.

12. The method of claim 1, wherein the carrier comprises one or more of a carbohydrate, an amino acid, a salt, a buffer, an alcohol, a polyalcohol, or a mixture thereof.

13. The method of claim 1, wherein the nanoparticles are administered at a concentration of about 10 ppb to about 100 ppm.

14. A method for treating a bacterial respiratory infection in a patient with cystic fibrosis and a thick mucus layer in the patient's lungs caused by cystic fibrosis, the method comprising:
   administering a treatment composition to the patient with cystic fibrosis via inhalation into the patient's lungs, wherein the patient's lungs contain a thick viscous mucus layer caused by cystic fibrosis and the bacterial respiratory infection is caused by bacteria, with the proviso that the bacterial respiratory infection is not caused by methicillin-resistant *Staphylococcus aureus* or *Pneumocyslis*, wherein the bacteria causing the bacterial respiratory infection are located in both the thick viscous mucus layer and in infected respiratory tissue, and wherein the treatment composition comprises:
      nonionic, ground state, non-crystalline spherical silver nanoparticles having no external edges or bond angles and that do not release silver ions, wherein the nanoparticles have a mean diameter in a range of about 1 nm to about 20 nm and a particle size distribution such that at least 99% of the silver nanoparticles have a diameter within 30% of the mean diameter, wherein the nanoparticles are uncoated, and
      a carrier formulated for administration via inhalation, wherein the carrier comprises a saline solution and at least one of a carbohydrate, amino acid, buffer, alcohol, or polyalcohol, and
   the treatment composition treating the bacterial respiratory infection by the silver nanoparticles penetrating the thick viscous mucus layer, reaching the infected respiratory tissue, and killing the bacteria causing the bacterial respiratory infection in both the thick viscous mucus layer and the infected respiratory tissue without the release of silver ions.

15. The method of claim 14, wherein the treatment composition is administered to the patient via inhalation using a metered-dose inhaler.

16. The method of claim 14, wherein the treatment composition is administered to the patient via inhalation using a nebulizer.

17. A method for treating a bacterial respiratory infection caused by Burkholderia cepacia complex in a cystic fibrosis patient having a thick mucus layer in the patient's lungs caused by cystic fibrosis, the method comprising:

administering a treatment composition to the cystic fibrosis patient via inhalation into the patient's lungs, wherein the patient's lungs contain a thick viscous mucus layer caused by cystic fibrosis and the bacterial respiratory infection is caused by *Burkholderia cepacia* complex, and wherein the bacterial respiratory infection is not caused by methicillin-resistant *Staphylococcus aureus* or *Pneumocyslis*, wherein the *Burkholderia cepacia* complex causing the bacterial respiratory infection is located in both the thick viscous mucus layer and in infected respiratory tissue, and wherein the treatment composition comprises:

nonionic, ground state, spherical silver nanoparticles having a mean diameter in a range of about 4 nm to about 12 nm and a particle size distribution such that at least 99% of the silver nanoparticles have a diameter within 30% of the mean diameter, wherein the nanoparticles are non-crystalline with no external edges or bond angles and are uncoated, and a carrier formulated for administration via inhalation, and the treatment composition treating the bacterial respiratory infection by the silver nanoparticles penetrating the thick viscous mucus layer, reaching the infected respiratory tissue, and killing the *Burkholderia cepacia* complex causing the bacterial respiratory infection in both the thick viscous mucus layer and the infected respiratory tissue without the release of silver ions.

18. The method of claim 17, wherein the nonionic, ground state, spherical silver nanoparticles have a mean diameter of about 6 nm to about 10 nm.

19. The method of claim 17, wherein the nonionic, ground state, spherical silver nanoparticles have a concentration of about 200 ppb to about 20 ppm by weight of the treatment composition.

20. The method of claim 17, wherein the nonionic, ground state, spherical silver nanoparticles have a concentration of about 500 ppb to about 10 ppm by weight of the treatment composition.

* * * * *